(12) United States Patent
Wood et al.

(10) Patent No.: US 12,173,012 B2
(45) Date of Patent: Dec. 24, 2024

(54) INDOLOCARBAZOLE ANALOGS OF STAUROSPORINE AND METHODS OF SYNTHESIS THEREOF

(71) Applicant: BAYLOR UNIVERSITY, Waco, TX (US)

(72) Inventors: John L. Wood, Waco, TX (US); Ke Kong, Rockville, MD (US); Kevin Gayler, Waco, TX (US)

(73) Assignee: BAYLOR UNIVERSITY, Waco, TX (US)

( * ) Notice: Subject to any disclaimer, the term of this patent is extended or adjusted under 35 U.S.C. 154(b) by 0 days.

(21) Appl. No.: 18/422,175

(22) Filed: Jan. 25, 2024

(65) Prior Publication Data

US 2024/0287095 A1    Aug. 29, 2024

Related U.S. Application Data

(62) Division of application No. 17/363,370, filed on Jun. 30, 2021, now Pat. No. 11,993,611.

(60) Provisional application No. 63/047,341, filed on Jul. 2, 2020.

(51) Int. Cl.
   *C07D 498/22*   (2006.01)
   *A61P 35/00*    (2006.01)

(52) U.S. Cl.
   CPC ............ *C07D 498/22* (2013.01); *A61P 35/00* (2018.01)

(58) Field of Classification Search
   CPC .................................................... C07D 498/22
   See application file for complete search history.

(56) References Cited

U.S. PATENT DOCUMENTS 6,037,468 A * 3/2000 Wood ...................... C07C 45/68
                                                              540/545

* cited by examiner

*Primary Examiner* — Laura L Stockton
(74) *Attorney, Agent, or Firm* — Jackson Walker LLP

(57) ABSTRACT

Equipotent indolocarbazole-derived analogs of staurosporine identified herein are prepared through C—H borylation chemistry. Functionality resides at C2 and C10 of the indolocarbazole aromatic region. Introducing functionality in this previously inaccessible region does not abrogate kinase activity and is shown to change the selectivity profile.

6 Claims, 11 Drawing Sheets

FIG. 6

Table 1. Analogs of Staurosporine.

| Entry | SM | R¹ | R² | R³ | Condition | Product | R¹ | R² | R³ | Yield |
|---|---|---|---|---|---|---|---|---|---|---|
| 1 | 8 | Bpin | H | H | A [a] | 13 | OH | H | H | 26% |
|   | 9 | H | Bpin | H | A | 14 | H | OH | H | 10% |
| 2 | 10 | H | H | Bpin | A | 15 | H | H | OH | 21% |
| 3 | 11 | Bpin | H | Bpin | A | 16 | OH | H | OH | 12% |
|   | 12 | H | Bpin | Bpin | A | 17 | H | OH | OH | 24% |
| 4 | 8 | Bpin | H | H | B [b] | 18 | OMe | H | H | 52%[c] |
|   | 9 | H | Bpin | H | B | 19 | H | OMe | H | [c] |
| 5 | 11 | Bpin | H | Bpin | B | 20 | OMe | H | OMe | 23%[d] |
|   | 12 | H | Bpin | Bpin | B | 21 | H | OMe | OMe | [d] |
| 6 | 8 | Bpin | H | H | C[e] | 22 | Cl | H | H | 20% |
|   | 9 | H | Bpin | H | C | 23 | H | Cl | H | 51% |
| 7 | 11 | Bpin | H | Bpin | C | 24 | Cl | H | Cl | 30% |
|   | 12 | H | Bpin | Bpin | C | 25 | H | Cl | Cl | 48% |

[a] Condition A: 1) NaBO₃, H₂O:THF (1:1), 25 °C, 2) TFA:DCM (2:3), 25 °C; [b] Condition B: 1) NaBO₃, H₂O:THF (1:1), 25 °C, 2) MeI, K₂CO₃, THF, 40 °C 3) TFA:DCM (1:4), 25 °C; [c] Combined yield of 18 and 19 in 1:2.3 ratio determined by ¹H NMR; [d] Combined yield of 20 and 21 in 1:1.4 ratio determined by ¹H NMR; [e] Condition C: 1) CuCl₂, H₂O:MeOH (1:1), 70 °C, 2) TFA:DCM (1:4), 25 °C; TFA = trifluoroacetic acid, DCM = dichloromethane, Bpin = pinacol boronic ester

INDOLOCARBAZOLE ANALOGS OF STAUROSPORINE AND METHODS OF SYNTHESIS THEREOF This application is a divisional of and claims priority to U.S. patent application Ser. No. 17/363,370, entitled "Indolocarbazole Analogs of Staurosporine," filed Jun. 30, 2021, which claims priority to U.S. Provisional Patent Application Ser. No. 63/047,341 entitled "Indolocarbazole Analogs of Staurosporine," filed Jul. 2, 2020, the entire contents of which are hereby incorporated by reference.

STATEMENT REGARDING FEDERALLY SPONSORED RESEARCH OR DEVELOPMENT

This invention was made with government support under R01 GM136759 awarded by the National Institutes of Health, and CHE1764240 awarded by the National Science Foundation. The government has certain rights in the invention.

BACKGROUND

The present disclosure relates to indolocarbazole analogs of staurosporine.

Staurosporine, isolated in 1977 from *Streptomyces staurosporeus*, exhibits potent inhibitory properties against a vast majority of the human kinome. Since its isolation, numerous drug discovery efforts have attempted to capitalize on the potency of staurosporine and several other naturally occurring indolocabazole-containing natural products (ICZs) through the preparation of semisynthetic analogs. The ICZ moiety of staurosporine has been demonstrated to play a key role in binding to the adenosine triphosphate (ATP) pocket of kinases, and thus, modifications to this core have been central to many structure-activity relationships (SAR) studies performed in hopes of improving both selectivity and potency. Although the homologous nature of the ATP binding sites in the human kinome has made the former quite challenging, several compounds have moved into clinical trials (e.g., CEP-1347) and at least one (e.g., Midostaurin) has been approved for use in cancer treatment.

Modifications of staurosporine have been reported, but due to limitations in available chemical methods, the C—H bonds in the indolocarbazole core have been resistant to derivatization.

SUMMARY

The present disclosure pertains to indolocarbazole analogs of staurosporine and their methods of synthesis.

FIG. 1 shows the structure of staurosporine and previous-identified analogs Midostaurin and CEP-1347.

Recently developed chemical methods have allowed for the preparation of indolocarbazole analogs of staurosporine that were previously inaccessible. The approach entails direct aromatic C—H functionalization to provide regioisomeric boronate intermediates, which in turn serve as diversification points from which various aromatically substituted staurosporine analogs can be accessed. The new staurosporine compounds, exemplified by the analogs disclosed here, have important therapeutic properties.

FIG. 2A shows a synthetic scheme used previously involving reactions on staurosporine. In previous SAR efforts seen in this scheme, the primary strategy taken in the semisynthetic preparation of ICZ-analogs has involved electrophilic aromatic substitution (EAS) chemistry, which has led to the development over one-thousand analogs of staurosporine and related ICZs. However, without exception the regiochemical outcome of EAS chemistry in these studies has been limited by the electronic effects of the heteroaromatic ring system and provides access to only two locations for substitution. As illustrated, this reactivity profile has limited functionalization to the upper half of the ICZ moiety, thus there are no biological studies of synthetic analogs possessing functionality at C2 and C10. In fact, the natural product TAN-999, which possesses a methoxy substituent at C10, is the only compound falling into this latter category that has been reported and was studied in the context of its immunomodulatory properties.

As part of an effort to fill the void in SAR studies of staurosporine's ICZ core, C—H activation borylation chemistry was investigated as an orthogonal approach to EAS chemistry. FIG. 2B shows a synthetic scheme for C—H activation borylation on staurosporine in accordance with preferred embodiments described herein. In contrast to EAS, which provides regiochemical outcomes primarily dictated by the electronic effects of an aromatic ring, the regioselectivity of C—H activation borylation is primarily influenced by steric congestion around the C—H bond. In addition to providing access to regions of staurosporine that have yet to be investigated from an SAR standpoint, this chemistry also furnishes intermediate boronic esters which are exceedingly malleable with regard to subsequent transformations.

Initial attempts to introduce a boronic ester employing staurosporine as substrate were unsuccessful, showing no signs of reaction despite high catalyst loadings, high temperatures, and reaction times spanning a few days. FIG. 3 shows a synthetic scheme attempted for borylation of staurosporine, where Boc=tert-Butyloxycarbonyl. Initially the lack of borylation was attributed to the poor solubility of staurosporine in solvents suitable for C—H activation borylation, such as THF or dioxane. To improve the solubility known N-Boc-carbamate 6 was prepared which was found to be readily soluble in THF. Disappointingly, 6 required the use of superstoichiometric quantities of the active iridium complex, lengthy reaction times, and high temperatures, to produce trace quantities of borylation products as observed by LC-MS analysis.

Having ruled out issues with reaction heterogeneity, the next aim was to address the Lewis basicity of the amine and lactam. Coordination of strongly Lewis basic moieties to the iridium catalyst has been demonstrated to be problematic due to formation of an inactive 18e$^-$ iridium complex. To circumvent this potential problem both the amine and the lactam were protected with a Boc group to furnish 7. With 7 in hand, borylation of this substrate proceeded to about 50% conversion (LC-MS monitoring) when using 4,4'diter-tbutyl 2,2' bipyridine ligand (DtBpy).

Based on this initial success, a ligand screen was performed that included: Binap, TolBinap, DM-Segphos, 2,2' bipyridine (Bpy), 4,4'dimethoxy 2,2' bipyridine (MeO$_2$Bpy), DtBpy, 2,2' bipyridine (Bpy), neocuproine, 3,4,7,8 tetramethyl 1, 10 Phen (Me$_4$Phen), and 1, 10 Phen. This effort revealed that employing the Phen ligand, THF as solvent, and heating to 100° C. in a sealed tube for 6 h gave the best conversion, producing three mono-borylated products, 8, 9, and 10, as well as, two bis-boronic esters, 11 and 12. FIG. 4 shows a synthetic scheme for the borylation of Bis-Boc Staurosporine 7 and preparation of Boron Pinacol Esters 8, 9, 10, 11 and 12, where DMAP=4-dimethylaminopyridine, TEA=triethylamine, COD=1,5-cyclooctadiene, Phen=1,10-phenanthroline, B$_2$Pin$_2$=bis(pinacolato)diboron, BPin=pinacolato borane. Notably reaction times longer than 6 h led to decomposition of the products as observed by LC-MS monitoring. After purification of the crude reaction mixture, mixtures of 8/9 and 11/12 were isolated in 31% and 33% yield, respectively, along with pure 10 in 4% yield. Attempts to make regiochemical assignments at this stage were hampered by significant overlap and broadening of the peaks in the $^1$H NMR due to the rotameric nature of the protecting groups. Thus, the respective mixtures were advanced in hopes of finding a method for separating the derived analogs.

To the latter end, the focus turned toward functionalizing 8-12 by exploring reactivity under oxidation and chlorination conditions, two known transformations of boronic esters, which were chosen for their robustness. FIG. 5 shows a strategy for analog synthesis. Additionally, it was speculated that the derived phenols and chlorides would allow a quick probe into the biological impact of their respective hydrogen bond donating and accepting properties. In the event, the boronic esters in 8-12 were transformed to the corresponding phenols by exposure to NaBO$_3$. Fortunately, after deprotecting the Boc groups under TFA conditions, the derived phenol regiomers 13-17 were separated. Applying this same sequence to the mixtures of 8/9 and 11/12 but including a methylation step (MeI) prior to Boc deprotection, furnished the corresponding methyl ethers 18-21 which, in contrast to their parent phenols, proved recalcitrant toward to separation. Turning next to the chloride analogs, halogenation chemistry developed by Kabalka and Hartwig was employed. To this end, exposure of the Bpin analogs 8/9 and 11/12 to CuCl$_2$ furnished intermediate aryl chlorides which, upon Boc deprotection, provided separable mixtures of 22/23 and 24/25 respectively.

BRIEF DESCRIPTION OF DRAWINGS

FIG. 6 shows a table of staurosporine analogs in accordance with preferred embodiments disclosed herein.

DETAILED DESCRIPTION OF PREFERRED EMBODIMENTS

The present disclosure relates to analogs of staurosporine. In preferred embodiments, the staurosporine analogs have the following structure:

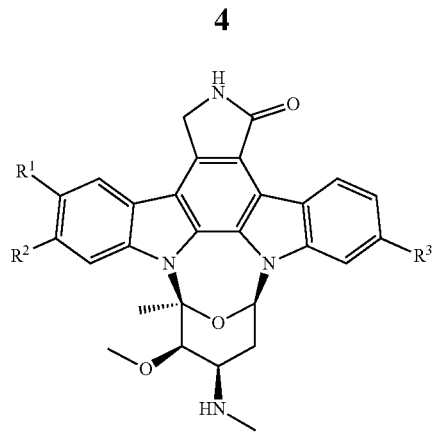

where $R_1$, $R_2$, and $R_3$ are each independently OH, H, OMe (OCH$_3$), or Cl.

Figure 7A:
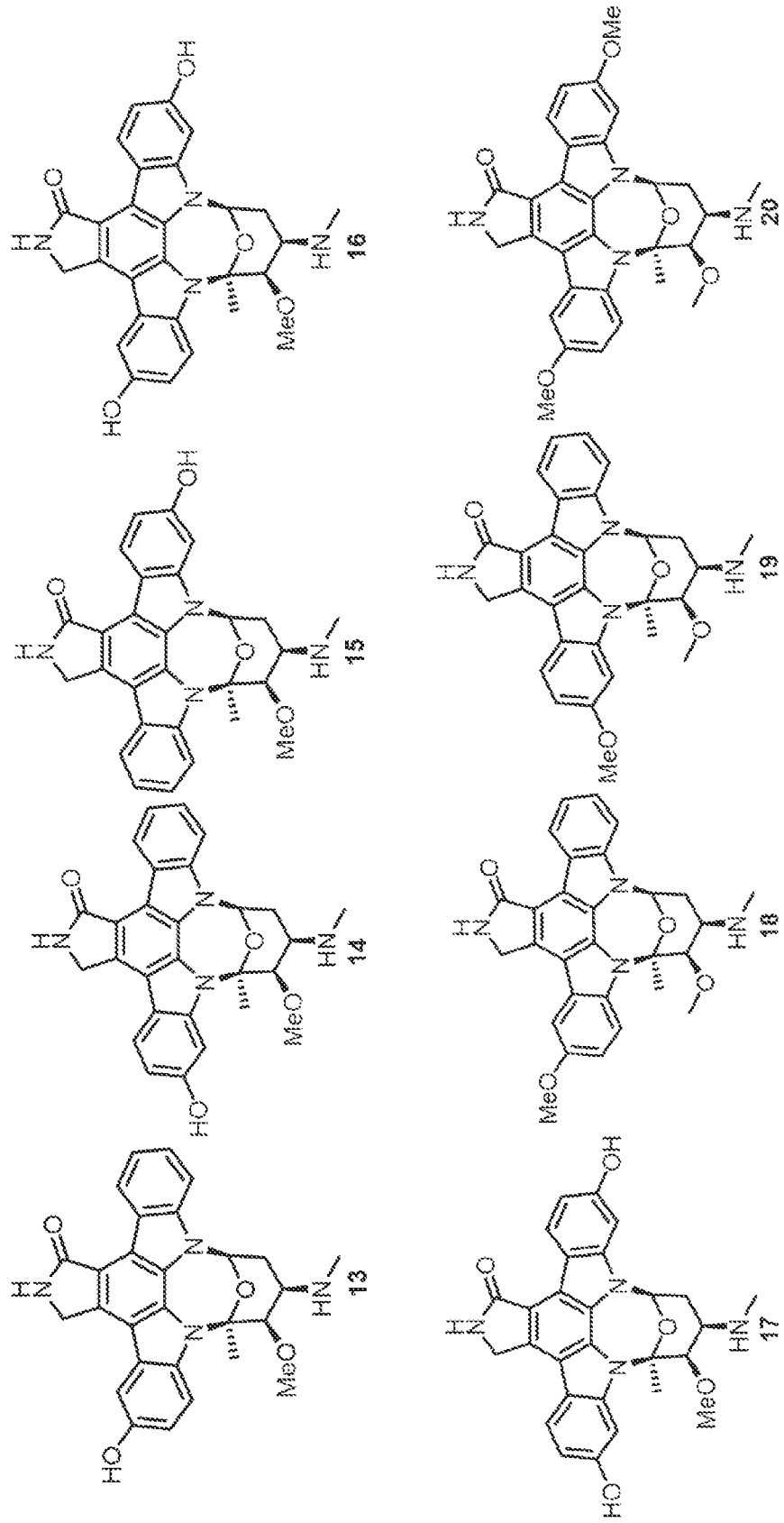
FIGS. 7A and 7B show structures of exemplary staurosporine analogs in accordance with preferred embodiments disclosed herein.
Figure 7B:
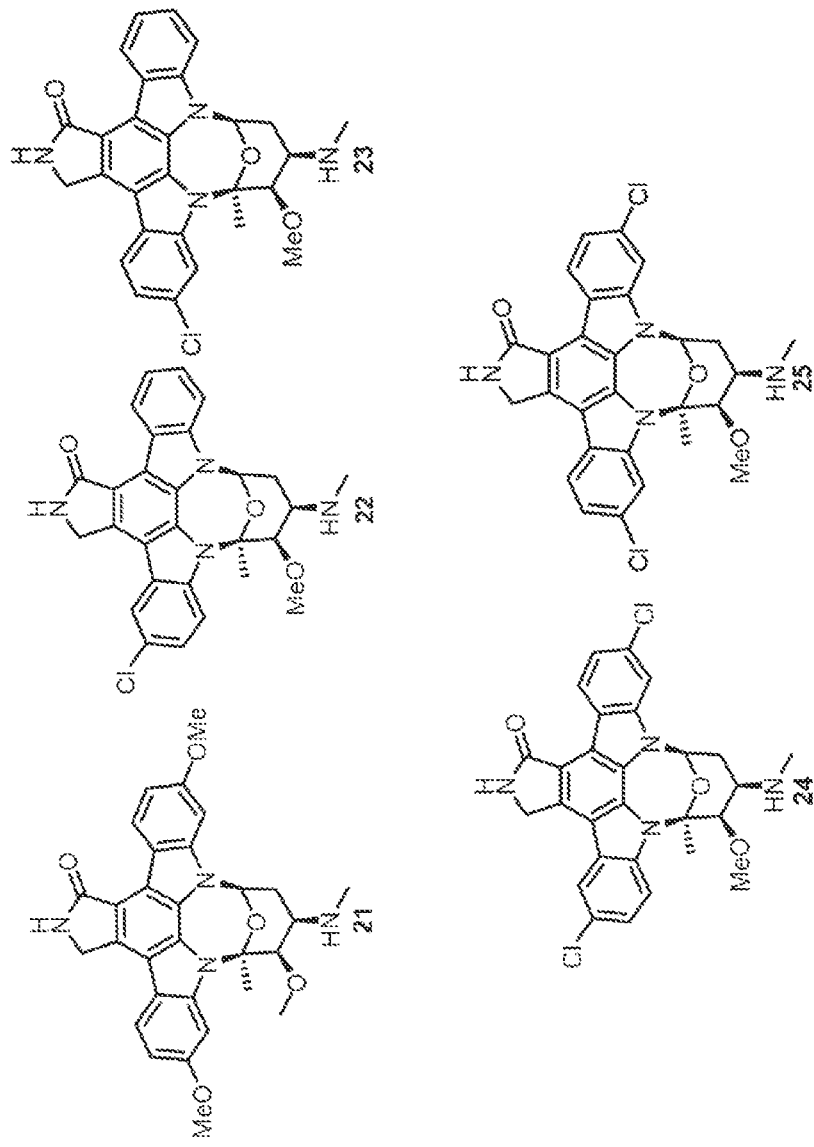

In further preferred embodiments, the staurosporine analogs are those identified in FIG. 6, which shows a table of analogs of staurosporine that have been synthesized. In additional preferred embodiments, the staurosporine analogs are those shown in FIGS. 7A and 7B.

The preferred embodiments of staurosporine analogs disclosed herein were accessed using a developed method wherein functionality resides at C2 and C10 of the indolocarbazole aromatic region. This methodology allows for the preparation of many new staurosporine analogs and potentially opens the door to further improvements in the kinase specificity profile manifest by this class of molecules. In addition, viability of the method was confirmed by the preparation of 13 analogs of staurosporine and, in a biological study, it was determined that introducing functionality in this previously inaccessible region does not abrogate kinase activity and indeed changes the selectivity profile.

The exemplary staurosporine analogs described herein may occur in different geometric and enantiomeric forms, and both pure forms and mixtures of these separate isomers are included in the scope of this invention, as well as any physiologically functional or pharmacologically acceptable salt derivatives or prodrugs thereof. Production of these alternate forms would be well within the capabilities of one skilled in the art.

The current invention also pertains to methods of prevention or therapy for protein kinase related diseases or conditions such as inflammatory and autoimmune conditions, cancer, mood disorders, and cardiovascular diseases, including the step of administering a preferred staurosporine analog compound in accordance with preferred embodiments disclosed herein. In preferred embodiments, the methods of prevention or therapy for protein kinase related diseases or conditions include the step of administering a compound that is a compound identified in FIG. 6 or FIG. 7.

In another aspect of the present invention there is provided a pharmaceutical composition including a therapeutically effective amount of staurosporine analog and a pharmaceutically acceptable excipient, adjuvant, carrier, buffer or stabiliser. A "therapeutically effective amount" is to be understood as an amount of an exemplary staurosporine analog that is sufficient to show a positive biological effect on a protein kinase related disease or condition being treated. The actual amount, rate and time-course of administration will depend on the nature and severity of the disease being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, or by injection, such as cutaneous, subcutaneous, or intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as sodium chloride solution, Ringer's solution, or lactated Ringer's solution. Preservatives, stabilisers, buffers, antioxidants and/or other additives may be included as required.

In another aspect, there is provided the use in the manufacture of a medicament of a therapeutically effective amount of a staurosporine analog as defined above for administration to a subject.

In another aspect, preferred embodiments described herein relate to a method for synthesizing staurosporine analogs. The method comprises a step of reacting staurosporine with $Boc_2O$ to produce Bis-Boc staurosporine, where Boc is tert-Butyloxycarbonyl. Another step includes reacting the Bis-Bos staurosporine with $B_2Pin_2$ to produce boron pinacol esters of Bis-Boc staurosporine, where $B_2Pin_2$ is bis(pinacolato)diboron. A further step in preferred embodiments of the method includes oxidizing or chlorinating the boron pinacol esters of Bis-Boc staurosporine to produce staurosporine analog intermediates. An optional step that may be performed in preferred embodiments of the method is the methylation of at least one phenol in the staurosporine analog intermediates. An additional step is deprotecting the staurosporine analog intermediates to remove Boc to produce the staurosporine analogs.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a nontoxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

Further aspects of the present invention will become apparent from the following description given by way of example only.

Example 1

Methods for synthesizing intermediate compounds and preferred embodiments of the staurosporine analogs are described in this example.

Unless otherwise stated all reactions were run using reagents as received from the manufacturers. The reactions were monitored by normal phase thin-layer chromatography (TLC) using Millipore glass-backed 60 Å plates (indicator F-254, 250 μM). Reactions were also monitored by a Waters Acquity UPLC-MS equipped with a UPLC BEH C18 1.7 μm (2.1×50 mm) column, using $H_2O$:MeCN plus 0.5% FA with a 95_5 to 10_90 gradient over 9 min.

Tetrahydrofuran and dichloromethane were dried using a solvent purification system manufactured by SG Water U.S.A., LLC. Manual flash chromatography was preformed using the indicated solvent systems with Silicycle SiliaFlash® P60 (230-400 mesh) silica gel as the stationary phase. Flash Chromatography on a Teledyne RF+UV-Vis Ms Comp MPLC was preformed using the indicated solvent systems, and Teledyne RediSep® Rf normal phase disposable columns of the indicated size and at the indicated flow rate.

Normal Phase Prep HPLC was performed with the indicated solvent system and 10 mL/min flow rate using a Sunfire Silica Prep 10 μM (10×250 mm) column.

Reverse Phase Prep HPLC was performed with the indicated solvent system at 10 mL/min flow rate using equipped with Gemini 5 μM C18 110 Å (100×21.2 mm) column.

Figure 1:
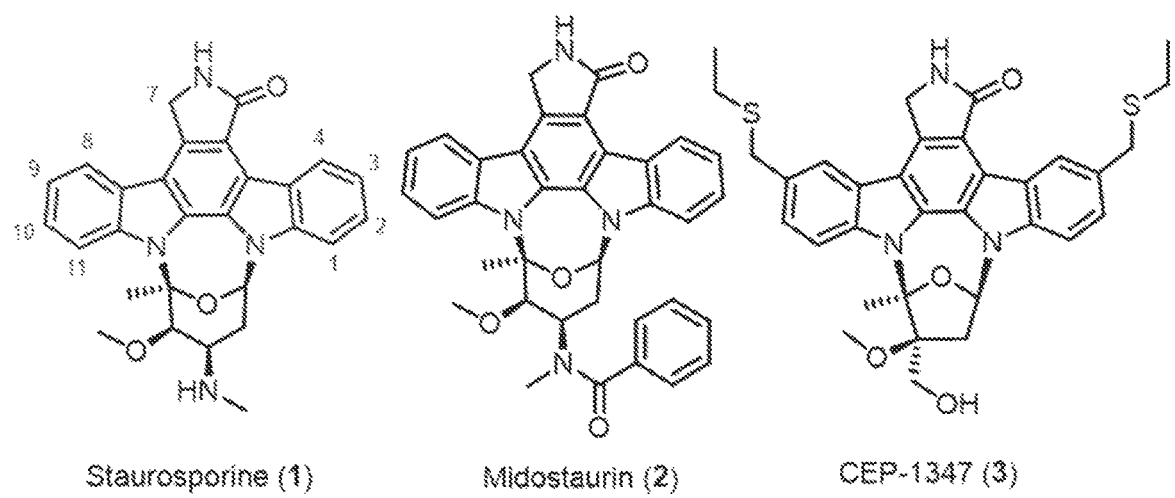
FIG. 1 shows the structure of staurosporine and previous-identified analogs Midostaurin and CEP-1347.
Figure 2A:
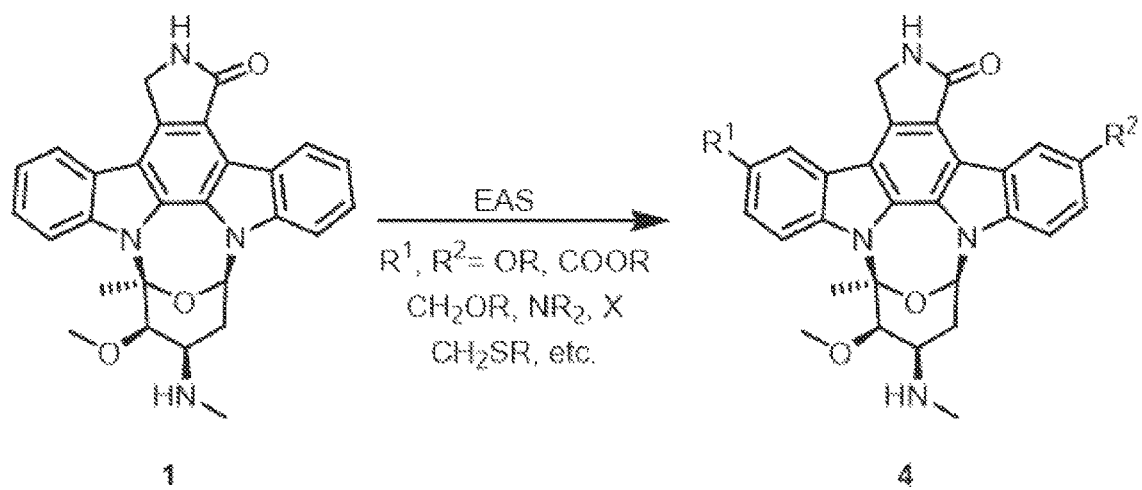
FIG. 2A shows a synthetic scheme used previously involving reactions on staurosporine.
Figure 2B:
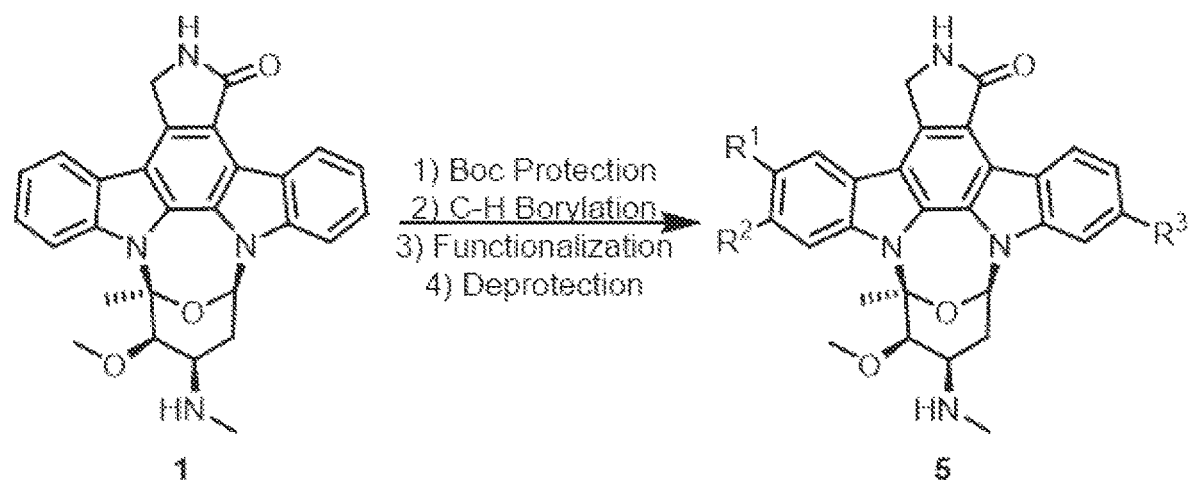
FIG. 2B shows a synthetic scheme for C—H activation borylation on staurosporine in accordance with preferred embodiments described herein.
Figure 3:
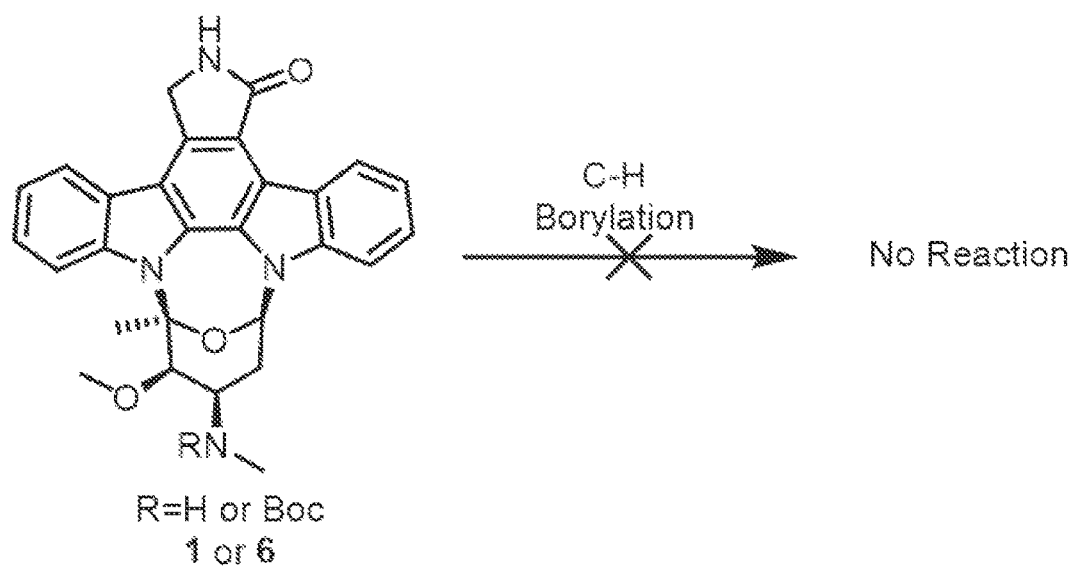
FIG. 3 shows a synthetic scheme attempted for borylation of staurosporine, where Boc=tert-Butyloxycarbonyl.
Figure 4:
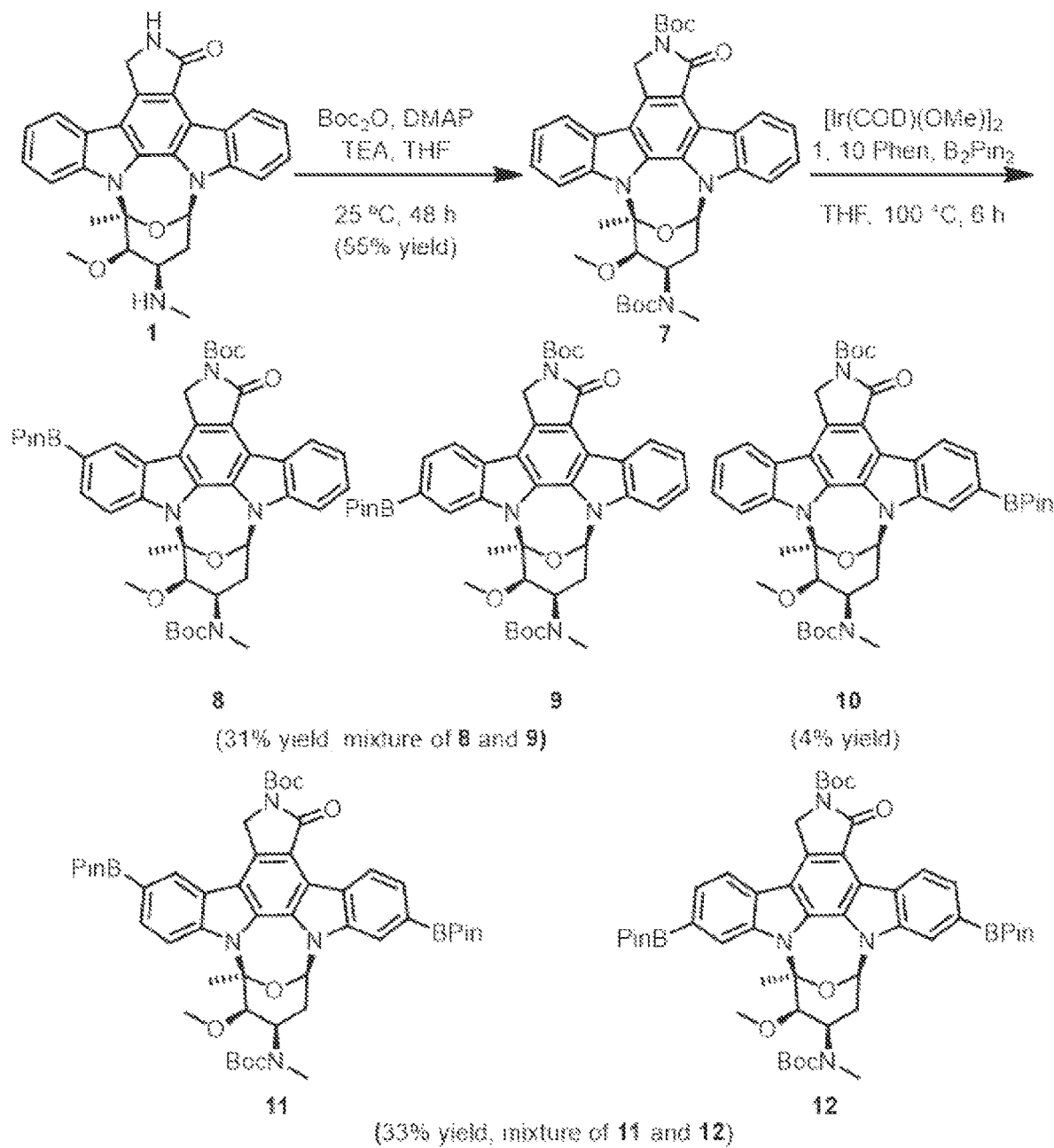
FIG. 4 shows a synthetic scheme for the borylation of Bis-Boc Staurosporine and the preparation of Boron Pinacol Esters.
Figure 5:
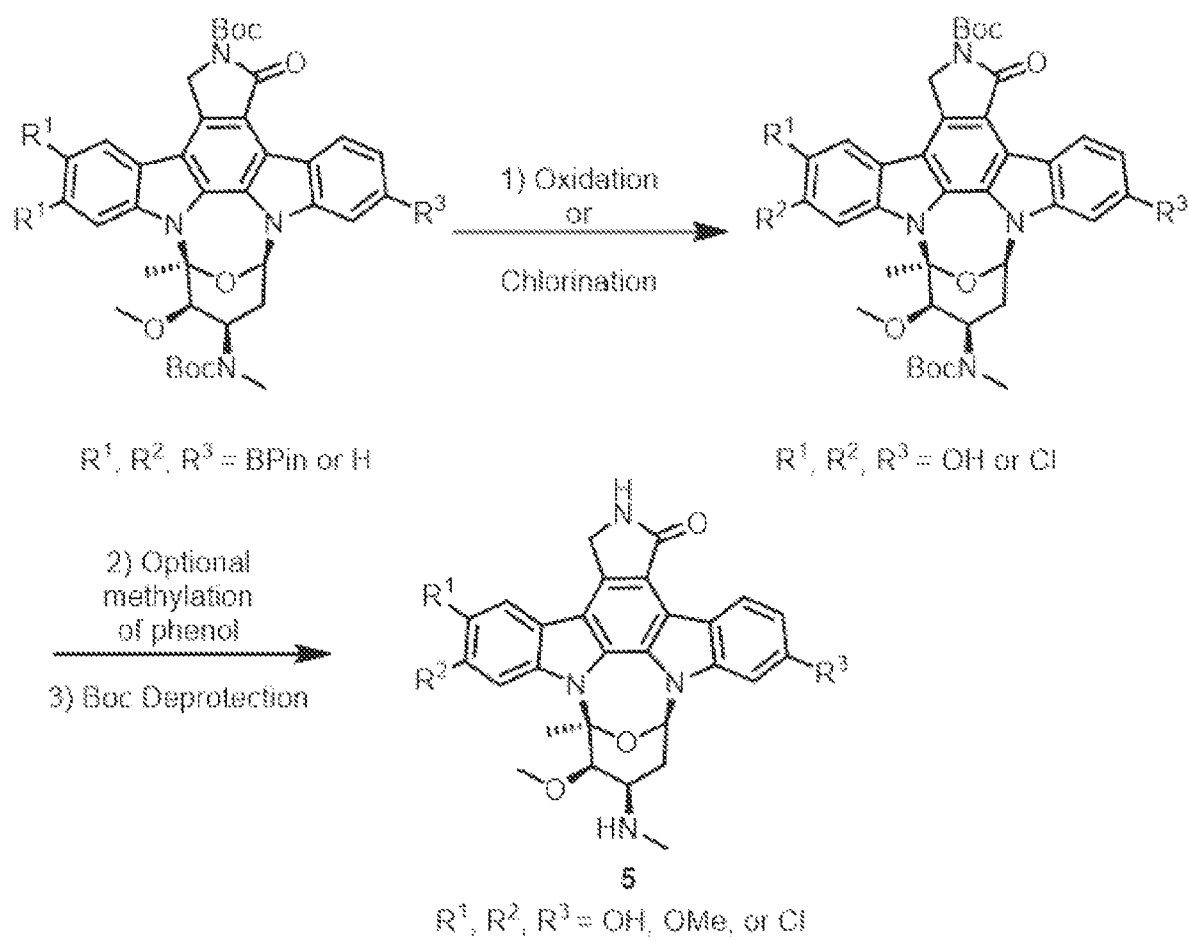
FIG. 5 shows a strategy for synthesis of staurosporine analogs in accordance with preferred embodiments disclosed herein.

1H and 13C NMR spectra were recorded on a Bruker Ascend™ 400 autosampler or a Bruker Ascend™ 600 autosampler. Chemical shifts (δ) are reported in parts per million (ppm) relative to the residual solvent resonance and coupling constants (J) are reported in hertz (Hz). NMR peak pattern abbreviations are as follows: s=singlet, d=doublet, dd=doublet of doublets, t=triplet, at =apparent triplet, q=quartet, ABq=AB quartet, m=multiplet. NMR spectra were calibrated relative to their respective residual NMR solvent peaks, $CDCl_3$=7.27 ppm (H NMR)/77.16 ppm (C NMR), MeOH=3.31 ppm (H NMR), Acetone=2.05 (H NMR). IR spectra were recorded on Bruker Platinum-ATR IR spectrometer using a diamond window. High Resolution mass spectra (HRMS) were obtained in the Baylor University Mass Spectrometry Center on a Thermo Scientific LTQ Orbitrap Discovery spectrometer using +ESI and reported for the molecular ion ($[M+H]^+$ & $[M+Na]^+$ respectively). Preparation of Bis-Boc Staurosporine (7) (See FIG. 4):

A flame dried 25 mL flask under an atmosphere of nitrogen was charged with Staurosporine (1) (500 mg, 1.07 mmol, 1 equiv) and suspended in THF (5 mL). DMAP (130.6 mg, 1.07 mmol, 1 equiv), TEA (0.44 mL, 3.21 mmol, 3 equiv), and $Boc_2O$ (0.62 mL, 2.68 mmol, 2.5 equiv) was added to the suspension and stirred for 26.5 h at 25° C., when additional $Boc_2O$ (0.9 mL, 4.3 mmol, 4.05 equiv) was added and stirred for a total of 48 h. Volatiles were removed by rotary evaporation, and reaction was purified with automated flash chromatography using 24 g disposable silica gel cartridge using 30:70 to 100:0 EtOAc:Hex gradient, then 0:100 to 20:80 MeOH:DCM gradient to provide 363.6 mg of (7) as an off white solid.

Rotamer A: $^1$H NMR (600 MHZ, Chloroform-d) δ 9.47 (d, J=8.0 Hz, 1H), 7.99 (d, J=7.6 Hz, 1H), 7.76 (d, J=8.4 Hz, 1H), 7.50 (t, J=7.5 Hz, 2H), 7.39 (q, J=8.6, 7.4 Hz, 2H), 7.25 (s, 1H), 6.69-6.66 (m, 1H), 5.31 (d, J=16.4 Hz, 1H), 5.23 (d, J=16.6 Hz, 1H), 4.81 (d, J=13.0 Hz, 1H), 4.06 (s, 1H), 2.72 (s, 3H), 2.59 (s, 3H), 2.55 (s, 2H), 2.46 (s, 3H), 1.73 (s, 9H), 1.52 (s, 9H).

Rotamer B: $^1$H NMR (600 MHz, Chloroform-d) δ 9.47 (d, J=8.0 Hz, 1H), 7.99 (d, J=7.6 Hz, 1H), 7.76 (d, J=8.4 Hz, 1H), 7.50 (t, J=7.5 Hz, 2H), 7.39 (q, J=8.6, 7.4 Hz, 2H), 7.25 (s, 1H), 6.69-6.66 (m, 1H), 5.31 (d, J=16.4 Hz, 1H), 5.19 (s, 1H), 4.62 (d, J=6.3 Hz, 1H), 3.93 (s, 1H), 2.72 (s, 3H), 2.59 (s, 3H), 2.55 (s, 2H), 2.46 (s, 3H), 1.73 (s, 9H), 1.61 (d, J=10.5 Hz, 9H).

$^{13}$C NMR (151 MHz, Chloroform-d) δ 167.8, 156.1, 151.3, 139.1, 136.8, 131.6, 130.1, 127.1, 126.4, 125.9, 125.3, 124.8, 123.4, 121.7, 121.0, 120.3, 118.5, 116.6, 114.0, 112.9, 107.8, 94.9, 85.0, 82.9, 82.7, 80.4, 60.7, 50.0, 49.4, 30.5, 29.5, 28.6, 28.5.

+ESI-HRMS m/z: calc'd for [M+Na]+$C_{38}H_{43}N_4O_7Na^+$=667.3126, found $C_{38}H_{43}N_4O_7Na^+$=667.3121.

FTIR (Thin Film) 3271, 1673, 1601, 1503, 1454, 14727, 1342, 1296, 1165, 1094, 1035, 971, 900, 794, 753, 695, 635, 523, 419 cm$^{-1}$ Preparation of Boron Pinacol Esters 8, 9, 10, 11, and 12 (See FIG. 4):

To a flame dried 1.5 dram vial under an atmosphere of nitrogen was charged [Ir(COD)(OMe)]2 (29.4 mg, 0.044 mmol, 0.3 equiv) and 1, 10 phenanthroline (15.9 mg, 0.088 mmol, 0.6 equiv) and dried azeotropically with toluene. To a flame dried 1.5 dram vial under an atmosphere of nitrogen was charged B$_2$Pin$_2$ (112.7 mg, 0.444 mmol, 3 equiv) and dried azeotropically with toluene. To flame dried 15 mL seal tube under an atmosphere of nitrogen was charged with (7) (100 mg, 0.148 mmol, 1 equiv) and dried azeotropically with toluene. B$_2$Pin$_2$ was transferred as a solution in THF (2 mL) via syringe to the vial containing [Ir(COD)(OMe)]$_2$ and 1, 10 phenanthroline, and allowed to stir for 20 min. Then the catalyst solution was transferred to the 15 mL seal tube using a syringe, followed by addition of THF (2 mL) the catalyst solution vial and subsequent transfer to the sealed tube. The reaction mixture was heated to 100° C. for 6 h and allowed to cool to 25° C. Volatiles were removed by rotary evaporation, and reaction was subjected to automated flash chromatography using 12 g disposable silica gel cartridge using 0:100 to 40:60 EtOAc:Hex gradient to provide a mixture of five region isomers which was subjected to further purification by RP-HPLC.

Preparative RP-HPLC was used to provide initial separation using 5:95 H$_2$O:MeCN isocratic solvent system.

Provided (36.0 mg) 8 and 9 as a mixture of two compounds. Regiochemical assignment was made after functionalization and Boc deprotection. $^{13}$C NMR of mixture showed significant overlap amongst all peaks and 1H of mixture showed significant overlap amongst most peaks, however two distinct compounds could be identified in the 1H and are reported separately.

Preliminary Characterization of 8 and 9 as a Mixture:

$^1$H NMR (400 MHZ, Chloroform-d) δ 9.45 (d, J=7.7, 1H), 8.23 (s, 1H), 7.94 (t, J=6.1 Hz, 1H), 7.83 (d, J=7.5 Hz, 1H), 7.48 (q, J=8.2 Hz, 1H), 7.40-7.34 (m, 1H), 7.22 (dd, J=15.1, 8.2 Hz, 1H), 6.66 (dt, J=11.7, 5.8 Hz, 1H), 5.46-5.25 (m, 2H), 4.83 (d, J=8.7 Hz, 1H), 4.08 (d, J=13.6 Hz, 1H), 2.71 (s, 3H), 2.63-2.42 (m, 8H), 1.75 (s, 3H), 1.73 (s, 9H), 1.53 (s, 9H), 1.43 (s, 12H).

$^1$H NMR (400 MHZ, Chloroform-d) δ 9.45 (d, J=7.7, 1H), 8.43 (s, 1H), 7.94 (t, J=6.1 Hz, 1H), 7.73 (d, J=8.4 Hz, 1H), 7.48 (q, J=8.2 Hz, 1H), 7.40-7.34 (m, 1H), 7.22 (dd, J=15.1, 8.2 Hz, 1H), 6.66 (dt, J=11.7, 5.8 Hz, 1H), 5.16 (d, J=16.6 Hz, 1H), 4.67 (s, 1H), 3.96 (d, J=20.5 Hz, 1H), 2.71 (s, 3H), 2.63-2.42 (m, 8H), 1.75 (s, 3H), 1.73 (s, 9H), 1.53 (s, 9H), 1.43 (s, 12H).

$^{13}$C NMR (101 MHZ, Chloroform-d) δ 167.8, 167.7, 156.1, 156.0, 151.8, 151.3, 138.6, 136.7, 132.2, 131.6, 131.6, 130.4, 130.2, 128.8, 127.0, 125.9, 123.3, 123.3, 120.8, 120.3, 120.2, 119.2, 118.3, 116.7, 114.2, 113.8, 107.8, 107.8, 95.0, 84.9, 84.1, 84.0, 83.0, 82.9, 82.7, 82.6, 80.4, 60.4, 49.9, 49.5, 49.4, 30.4, 29.6, 29.5, 28.6, 28.5, 25.1, 25.1.

+ESI-HRMS m/z: calc'd for [M+H]+ $C_{44}H_{54}BN_4O_9^+$=793.3978, found $C_{44}H_{54}BN_4O_9^+$=793.3981.

FTIR (Thin Film) 2977, 2931, 1775, 1732, 1703, 1634, 1614, 1493, 1446, 1344, 268, 1215, 1144, 1111, 1082, 1044, 1019, 966, 856, 688

Provided 10 (5.1 mg) as a single compound. Regiochemical assignment was made after functionalization and Boc deprotection.

Preliminary Characterization of 10:

$^1$H NMR (400 MHZ, Chloroform-d) δ 9.45 (d, J=8.0 Hz, 1H), 8.02 (s, 1H), 7.83 (d, J=8.1 Hz, 1H), 7.79 (s, 1H), 7.75 (d, J=8.6 Hz, 1H), 7.51 (t, J=8.0 Hz, 1H), 7.40 (t, J=7.5 Hz, 1H), 6.81 (s, 1H), 5.34 (s, 2H), 4.81 (d, J=13.2 Hz, 1H), 4.70-4.49 (m, 1H), 4.12 (s, 1H), 2.72 (s, 6H), 2.59-2.47 (m, 2H), 2.44 (s, 3H), 1.73 (s, 9H), 1.52 (s, 9H), 1.42 (s, 12H).

$^{13}$C NMR (101 MHz, Chloroform-d) δ 151.2, 136.4, 131.5, 130.4, 126.4, 126.2, 125.8, 125.4, 121.7, 121.0, 114.4, 114.3, 113.1, 95.0, 84.9, 84.0, 83.0, 82.8, 61.0, 49.5, 29.8, 28.6, 28.5, 25.1, 25.1.

+ESI-HRMS m/z: calc'd for [M+H]+ $C_{44}H_{54}BN_4O_9^+$=793.3978, found $C_{44}H_{54}BN_4O_9^+$=793.3984.

FTIR (Thin Film) 2977, 296, 2855, 1772, 1733, 1700, 1446, 1367, 1342, 1283, 1259, 1224, 1144, 1109, 1082, 969

Provided (45.1 mg) 11 and 12 as a mixture of two compounds.

Regiochemical assignment was made after functionalization and Boc deprotection. $^1$H NMR of mixture shows significant overlap amongst the majority of the peaks, however two compounds could be identified, and $^1$H NMR peaks are reported separately.

Preliminary Characterization of 11 and 12 as a Mixture:

$^1$H NMR (400 MHZ, Chloroform-d) δ 9.45 (d, J=8.0 Hz, 1H), 8.22 (s, 1H), 8.00 (d, J=7.8 Hz, 1H), 7.83 (d, J=8.3 Hz, 2H), 7.81 (d, J=4.4 Hz, 1H), 6.88-6.76 (m, 1H), 5.36 (s, 2H), 4.84 (d, J=11.3 Hz, 1H), 4.16 (d, J=17.0 Hz, 1H), 2.73 (s, 3H), 2.51 (s, 3H), 2.44 (s, 3H), 1.74 (s, 9H), 1.64 (s, 2H), 1.54 (s, 9H), 1.42 (s, 12H), 1.42 (s, 12H).

$^1$H NMR (400 MHZ, Chloroform-d) δ 9.45 (d, J=8.0 Hz, 1H), 8.48 (s, 1H), 8.22 (s, 1H), 7.94 (d, J=8.5 Hz, 1H), 7.83 (d, J=8.3 Hz, 1H), 7.81 (d, J=4.4 Hz, 2H), 7.72 (d, J=8.2 Hz, 1H), 6.88-6.76 (m, 1H), 5.46 (s, 2H), 4.72-4.54 (m, 1H), 4.05 (d, J=21.2 Hz, 1H), 2.70 (s, 3H), 2.51 (s, 3H), 2.44 (s, 3H), 1.75 (s, 9H), 1.64 (s, 2H), 1.54 (s, 9H), 1.42 (s, 12H), 1.42 (s, 12H).

$^{13}$C NMR (101 MHZ, Chloroform-d) δ 167.8, 167.6, 156.1, 151.7, 151.3, 138.9, 136.4, 136.4, 132.0, 131.6, 131.4, 130.7, 130.5, 128.8, 127.0, 126.3, 126.2, 125.7, 124.4, 120.8, 119.6, 119.4, 118.6, 116.6, 114.7, 114.3, 114.3, 95.1, 84.8, 84.1, 84.0, 84.0, 83.2, 83.1, 82.8, 82.7, 80.4, 60.8, 50.1, 49.6, 49.5, 30.6, 29.9, 28.6, 28.5, 25.1, 25.1, 25.0.

+ESI-HRMS m/z: calc'd for [M+Na]+ $C_{50}H_{65}B_2N_4O_{11}Na^+$=919.4830, found $C_{50}H_{65}B_2N_4O_{11}Na^+$=919.4839.

FTIR (Thin Film) 2977, 2931, 1774, 1731, 1703, 1634, 1614, 1493, 1448, 1345, 1268, 1215, 1144, 1111, 1082, 1044, 1019, 966, 856, 688

Figure 8:
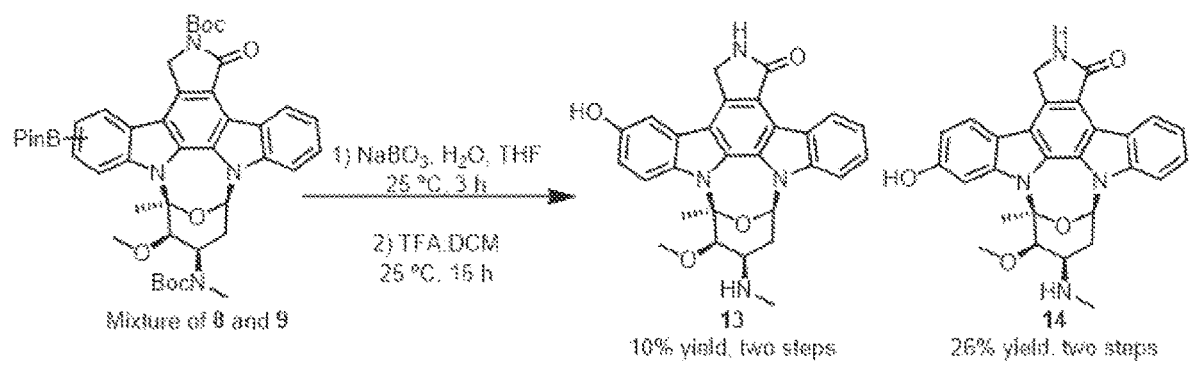
FIGS. 8-14 show schemes for the synthesis of representative staurosporine analogs in accordance with preferred embodiments disclosed herein.

Preparation of Phenols 13 and 14:

FIG. 8 shows a synthetic scheme for the preparation of phenols 13 and 14 from a mixture of 8 and 9.

To 1.5 dram vial was added a mixture of 8 and 9 (18.0 mg, 0.023 mmol, 1 equiv) as a solution in THF (1 mL), followed by the addition of $NaBO_3 \cdot 4\,H_2O$ (15.4 mg, 0.10 mmol, 4.5 equiv) and $H_2O$ (1 mL) and stirred at 25° C. for 3 h and reaction was diluted with $H_2O$, extracted with DCM, and organic layers were dried with $Na_2SO_4$. Half of the crude mixture was taken forward without further purification.

The above mixture was dissolved in DCM (150 µL), to which TFA (100 µL) was added and stirred for 16 h, and volatiles were evaporated. Preparative RP-HPLC was used for separation using 55:45 $H_2O$:MeCN with ammonium formate buffer at pH=9 isocratic solvent system. Samples with further purified using silica flash column chromatography using 0:100 to 5:95 to 10:90 MeOH:DCM.

Purification provided 2.9 mg of 13 as a white solid.

$^1$H NMR (600 MHZ, Methanol-$d_4$) δ 9.21 (d, J=7.9 Hz, 1H), 8.53 (brs, 2H), 7.72 (d, J=8.4 Hz, 1H), 7.43 (t, J=8.1 Hz, 1H), 7.39 (d, J=1.8 Hz, 1H), 7.31 (d, J=8.1 Hz, 1H), 7.26 (t, J=7.5 Hz, 1H), 6.88 (dd, J=8.4, 1.9 Hz, 1H), 6.60 (dd, J=8.3, 2.4 Hz, 1H), 4.88 (d, J=17.3 Hz, 1H), 4.80 (d, J=17.3 Hz, 1H), 4.18-4.14 (m, 1H), 3.67 (s, 1H), 2.99-2.92 (m, 1H), 2.68 (s, 3H), 2.42 (s, 3H), 2.37 (s, 3H), 2.34-2.29 (m, 1H).

$^{13}$C NMR (151 MHZ, Methanol-$d_4$) δ 175.5, 157.2, 141.6, 138.0, 133.0, 131.4, 128.0, 127.0, 126.2, 124.6, 122.9, 120.6, 119.8, 119.0, 116.2, 115.9, 109.1, 100.8, 93.8, 82.8, 82.2, 59.9, 54.5, 47.0, 32.3, 29.8, 29.2.*

*Missing 13C in aromatic region is observed in provided HMBC spectrum. Regiochemistry assigned by combination of 1H and NOESY provided and comparison to phenol 14.

+ESI-HRMS m/z: calc'd for [M+H]$^+$ $C_{28}H_{27}N_4O_4^+$=483.2027, $C_{28}H_{27}N_4O_4^+$ found=483.2037.

FTIR (Thin Film) 3297, 2980, 1663, 1654, 1646, 1591, 1488, 1465, 1419, 1395, 1376, 1347, 1316, 1251, 1208, 1151, 1125, 1076, 756

Purification provided 1.1 mg of 14 as a white solid.

$^1$H NMR (600 MHZ, Methanol-$d_4$) δ 9.24 (d, J=8.0 Hz, 1H), 8.58 (s, 1H), 7.83 (d, J=9.0 Hz, 1H), 7.48-7.45 (m, 1H), 7.39 (d, J=8.2 Hz, 1H), 7.34 (d, J=2.5 Hz, 1H), 7.30-7.26 (m, 1H), 7.02 (d, J=2.5 Hz, 1H), 6.69 (dd, J=8.0, 2.2 Hz, 1H), 4.93 (d, J=9.2 Hz, 2H), 4.15 (s, 1H), 3.64 (s, 1H), 2.98-2.91 (m, 2H), 2.75 (s, 3H), 2.42 (s, 3H), 2.40-2.34 (m, 2H), 2.30 (s, 3H).

$^{13}$C NMR (151 MHZ, Methanol-$d_4$) δ 175.5, 153.0, 138.1, 134.6, 134.3, 132.4, 128.0, 127.1, 126.8, 126.4, 124.6, 120.7, 119.4, 116.5, 115.4, 115.2, 109.2, 107.0, 93.7, 83.0, 82.2, 59.7, 57.5, 47.1, 32.5, 30.1, 29.4.*

*Missing 13C in aromatic region is observed in HMBC spectrum.

Regiochemistry assigned by $^1$H, COSY, HSQC, and HMBC provided and comparison to phenol 13.

+ESI-HRMS m/z: calc'd for [M+H]$^+$ $C_{28}H_{27}N_4O_4^+$=483.2027, $C_{28}H_{27}N_4O_4^+$ found=483.2037.

FTIR (Thin Film) 3249, 2950, 2813, 1663, 1654, 1593, 1458, 1388, 1348, 1321, 1258, 1204, 1151, 1120, 1072, 797, 759

Figure 9:
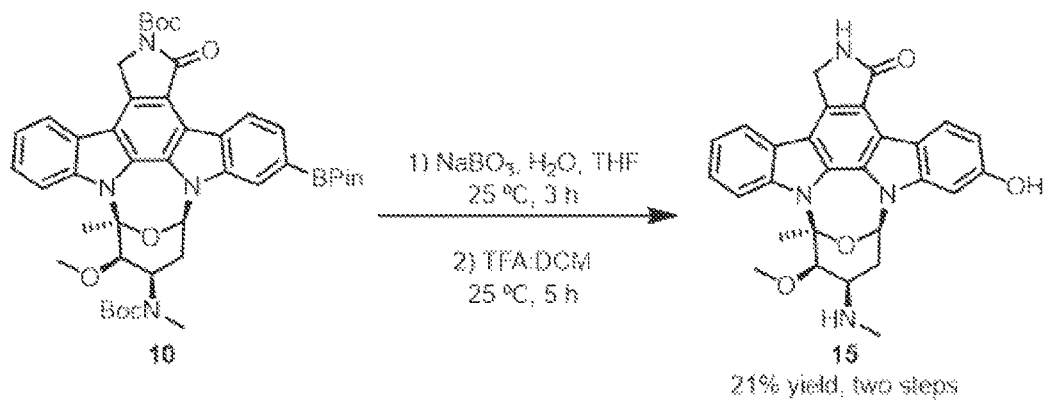

Preparation of Phenol 15:

FIG. 9 shows a synthetic scheme for the preparation of Phenol 15 from 10.

To 1.5 dram vial was added 10 (5.1 mg, 0.006 mmol, 1 equiv) as a solution in THF (0.5 mL), followed by the addition of $NaBO_3 \cdot 4\,H_2O$ (4.5 mg, 0.03 mmol, 4.5 equiv) and $H_2O$ (0.5 mL) and stirred at 25° C. for 1.5 h and reaction was diluted with $H_2O$, extracted with DCM, and organic layers were dried with $Na_2SO_4$. Crude material purified using silica flash column chromatography using 50:50 EtOAc:Hex to remove any unreacted stating material, and was taken forward to the next step.

The above mixture was dissolved in DCM (250 µL), to which TFA (100 µL) was added and stirred for 5 h, and volatiles were evaporated. Crude material purified using silica flash column chromatography using 0:100 to 5:95 to 10:90 MeOH:DCM, to provide 0.6 mg of 15 as a white solid.

$^1$H NMR (600 MHZ, Methanol-$d_4$) δ 9.02 (d, J=8.6 Hz, 1H), 7.98 (s, 1H), 7.95 (d, J=7.3 Hz, 1H), 7.44-7.40 (m, 1H), 7.33-7.29 (m, 1H), 6.80 (dd, J=8.6, 2.1 Hz, 1H), 6.77 (d, J=2.0 Hz, 1H), 6.54 (dd, J=7.0, 2.1 Hz, 1H), 4.99 (d, J=1.8 Hz, 2H), 4.57 (s, 1H), 4.09 (d, J=3.1 Hz, 1H), 3.07 (s, 3H), 2.73-2.66 (m, 2H), 2.50 (dd, J=6.8, 2.1 Hz, 1H), 2.48 (dd, J=6.7, 2.1 Hz, 1H), 1.95 (s, 3H).

$^{13}$C NMR (151 MHZ, Methanol-$d_4$) δ 174.4, 156.2, 139.4, 138.5, 132.2, 130.5, 126.6, 126.2, 124.5, 124.1, 120.5, 119.9, 117.4, 116.3, 115.7, 114.1, 113.2, 108.7, 93.3, 92.1, 80.8, 57.4, 51.7, 48.2, 45.8, 31.9, 29.4, 28.5.

Regiochemical Assignment made through $^1$H spectrum.

+ESI-HRMS m/z: calc'd for [M+H]$^+$ $C_{28}H_{27}N_4O_4^+$=483.2027, $C_{28}H_{27}N_4O_4^+$ found=483.2038.

FTIR (Thin Film): 3249, 2918, 2850, 1672, 1585, 1459, 1354, 1324, 1283, 1204, 1119, 826, 744

Figure 10:
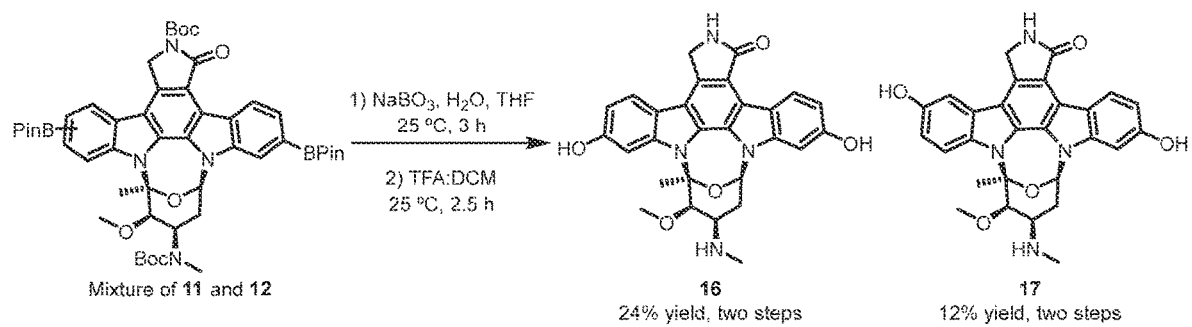

Preparation of Phenols 16 and 17:

FIG. 10 shows a synthetic scheme for the preparation of Phenols 16 and 17 from a mixture of 11 and 12.

To 1.5 dram vial was added a mixture of 11 and 12 (22.5 mg, 0.025 mmol, 1 equiv) as a solution in THF (1.5 mL), followed by the addition of $NaBO_3 \cdot 4\,H_2O$ (34.0 mg, 0.22 mmol, 9 equiv) and $H_2O$ (1 mL) and stirred at 25° C. for 7 h and reaction was diluted with $H_2O$, extracted with DCM, and organic layers were dried with $Na_2SO_4$. Half of the crude mixture was taken forward without further purification.

The above mixture was dissolved in DCM (250 µL), to which TFA (100 µL) was added and stirred for 2.5 h, and volatiles were evaporated. Preparative RP-HPLC was used for separation using 70:30 to 60:40 $H_2O$:MeCN with ammonium formate buffer at pH=9 gradient method. Samples were further purified using silica flash column chromatography using 0:100 to 5:95 to 10:90 to 20:80 MeOH:DCM.

Purification provided 1.5 mg of 16 as a white solid.

$^1$H NMR (600 MHZ, Methanol-$d_4$) δ 9.00 (d, J=8.7 Hz, 1H), 8.55 (s, 1H), 7.81 (d, J=9.0 Hz, 1H), 7.31 (d, J=2.4 Hz, 1H), 6.94 (dd, J=9.0, 2.5 Hz, 1H), 6.79 (dd, J=8.6, 2.1 Hz, 1H), 6.77 (d, J=2.1 Hz, 1H), 6.52 (dd, J=6.8, 2.0 Hz, 1H), 4.95 (d, J=2.9 Hz, 2H), 4.03 (d, J=3.2 Hz, 1H), 3.13 (s, 3H), 2.67-2.60 (m, 1H), 2.49 (dd, J=14.8, 7.2 Hz, 1H), 2.35 (s, 3H), 1.90 (s, 6H), 1.89 (s, 3H).

$^{13}$C NMR (151 MHZ, Methanol-$d_4$) δ 175.9, 157.5, 152.6, 139.8, 135.2, 133.8, 132.4, 127.9, 127.6, 126.7, 118.2, 117.8, 116.8, 116.3, 114.5, 114.3, 110.1, 106.6, 94.7, 93.3, 84.4, 82.2, 58.7, 52.9, 47.1, 33.5, 31.1, 30.0.

Regiochemical assignment made by $^1$H, Comparison to Phenol 13 and bis-phenol 17, and NOESY.

+ESI-HRMS m/z: calc'd for [M+H]$^+$ $C_{28}H_{27}N_4O_5^+$=499.1976, found $C_{28}H_{27}N_4O_5$+=499.1985.

FTIR (Thin Film): 3259, 1975, 1594, 1463, 1349, 1211, 1118

Purification provided 3.0 mg of 17 as a white solid.

$^1$H NMR (600 MHZ, Methanol-$d_4$) δ 8.98 (d, J=8.5 Hz, 1H), 7.73 (d, J=8.4 Hz, 1H), 7.41 (d, J=2.0 Hz, 1H), 6.83 (dd, J=8.4, 2.0 Hz, 1H), 6.78 (dd, J=8.5, 2.1 Hz, 1H), 6.75 (d, J=2.1 Hz, 1H), 6.49 (dd, J=6.8, 2.2 Hz, 1H), 4.93 (d, J=3.1 Hz, 2H), 4.02 (d, J=3.3 Hz, 1H), 3.18 (s, 3H), 2.65-2.59 (m, 1H), 2.51-2.47 (m, 1H), 2.34 (s, 3H), 1.87 (s, 3H).

*Note Doublet with integration of 1H is eclipsed by Methanol-$d_4$ peak.

$^{13}$C NMR (101 MHz, Methanol-$d_4$) δ 175.7, 157.5, 157.0, 141.6, 139.7, 132.6, 131.4, 127.9, 127.5, 122.8, 119.1, 118.9, 117.9, 116.6, 115.3, 110.9, 110.1, 100.8, 94.9, 93.8, 82.6, 82.1, 59.9, 54.6, 47.0, 32.2, 29.7, 29.1.

Regiochemical assignment made by $^1$H, Comparison to Phenol 14 and bis-phenol 16, and NOESY.

+ESI-HRMS m/z: calc'd for [M+H]$^+$ $C_{28}H_{27}N_4O_5^+$=499.1976, found $C_{28}H_{27}N_4O_5^+$=499.1986.

FTIR (Thin Film) 3239, 2334, 1650, 1591, 1461, 1425, 1348, 1214, 1119, 825

Figure 11:
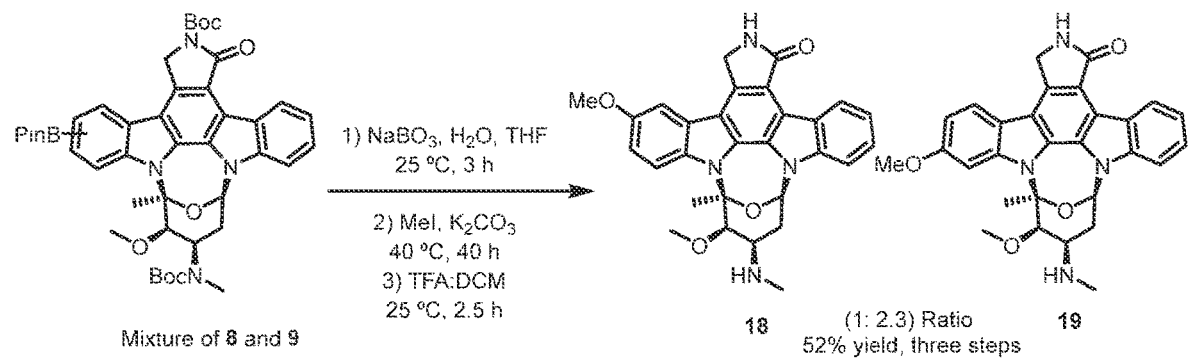

Preparation of Methyl Ethers 18 and 19:

FIG. 11 shows a synthetic scheme for the preparation of methyl esters 18 and 19 from a mixture of 8 and 9.

To 1.5 dram vial was added a mixture of 8 and 9 (18.0 mg, 0.023 mmol, 1 equiv) as a solution in THF (1 mL), followed by the addition of $NaBO_3 \cdot 4 H_2O$ (15.4 mg, 0.10 mmol, 4.5 equiv) and $H_2O$ (1 mL) and stirred at 25° C. for 3 h and reaction was diluted with $H_2O$, extracted with DCM, and organic layers were dried with $Na_2SO_4$. Half of the crude mixture was taken forward without further purification.

To a flame dried 1.5 dram vial under an atmosphere of nitrogen was added the crude mixture as a solution in THF (0.5 mL) followed by addition of $K_2CO_3$ (4.4 mg, 0.032 mmol, 2 equiv) and MeI (1.2 μL, 0.018 mmol, 1.1 equiv) and stirred at 25° C. for 2 h, the heated to 40° C. for 30 h, and allowed to cool followed by evaporation of volatiles. Reaction was dissolved in DCM, washed with water, and aqueous layer was extracted with DCM. Organic layers were dried with $Na_2SO_4$.

The crude mixture was taken forward without further purification.

The above mixture was dissolved in DCM (150 μL), to which TFA (100 μL) was added and stirred for 16 h, and volatiles were evaporated. The mixture was purified using silica flash column chromatography using 0:100 to 5:95 to 10:90 MeOH:DCM. To provide a 3.0 mg of 18:19 in a 1:2.3 ratio.

$^1$H NMR (600 MHZ, Methanol-$d_4$) δ 9.25 (s, 1H), 7.91 (d, J=9.2 Hz, 1H),), 7.48-7.39 (m, 1H), 7.27 (m, 2H), 7.08 (dd, J=9.2, 2.6 Hz, 1H), 6.65 (dd, J=8.8, 2.0 Hz, 1H), 5.01 (s, 2H), 4.03 (d, J=3.4 Hz, 1H), 3.95 (s, 3H), 3.17 (s, 3H), 2.66-2.60 (m, 1H), 2.59-2.53 (m, 1H), 2.36 (s, 3H), 1.78 (s, 3H)

Note* Doublet with integration of 1H is eclipsed by Methanol-$d_4$ peak.

$^1$H NMR (600 MHZ, Chloroform-d) δ 9.41 (d, J=7.5 Hz, 1H), 7.76 (d, J=8.5 Hz, 1H), 7.50-7.45 (m, 2H), 7.38-7.34 (m, 1H), 7.28 (d, J=7.7 Hz, 1H, 6.97 (dd, J=8.5, 2.1 Hz, 1H), 6.54 (d, J=5.6 Hz, 1H), 6.32 (s, 1H), 4.97 (d, J=5.2 Hz, 1H), 3.96 (s, 3H), 3.88 (d, J=3.4 Hz, 1H), 3.45 (s, 3H), 3.38-3.33 (m, 1H), 2.75 (d, J=3.9 Hz, 1H), 2.40 (dd, J=11.9, 5.8 Hz, 1H), 2.34 (s, 3H), 1.59 (s, 3H)

$^{13}$C NMR (151 MHz, Methanol-$d_4$) δ 175.7, 155.8, 142.2, 138.2, 134.4, 133.1, 132.5, 128.2, 127.0, 126.2, 122.4, 119.8, 116.6, 115.8, 114.4, 109.9, 109.0, 108.8, 104.6, 93.2, 84.4, 82.2, 58.6, 56.3, 52.9, 47.1, 33.4, 31.1, 30.1.

Regiochemistry and major product assigned by comparison of $^1$H NMR in Chloroform-d of the mixture to reported spectra of TAN-999.

+ESI-HRMS m/z: calc'd for [M+H]$^+$ $C_{29}H_{29}N_4O_4$=497.2183, found $C_{29}H_{29}N_4O_4$=497.2183.

FTIR (Thin Film): 3337, 2918, 2850, 2333, 1677, 1588, 1559, 1466, 1420, 1351, 1319, 1292, 1209, 1128, 1038, 802, 751, 724

$^1$H NMR (600 MHZ, Methanol-$d_4$) δ 9.23 (d, J=8.1 Hz, 1H), 7.83 (d, J=8.5 Hz, 1H), 7.52 (d, J=2.2 Hz, 1H), 7.48-7.39 (m, 2H), 7.27 (m, 1H), 6.97 (dd, J=8.5, 2.1 Hz, 1H), 6.63 (dd, J=6.5, 2.2 Hz, 1H), 4.96 (d, J=2.6 Hz, 2H), 4.07 (d, J=3.4 Hz, 1H), 3.95 (s, 3H), 3.24 (s, 3H), 2.66-2.60 (m, 1H), 2.59-2.53 (m, 1H), 2.37 (s, 3H), 1.78 (s, 3H).

Note* Doublet with integration of 1H is eclipsed by Methanol-$d_4$ peak.

$^1$H NMR (600 MHz, Chloroform-d) δ 9.41 (d, J=7.5 Hz, 1H), 7.76 (d, J=8.5 Hz, 1H), 7.50-7.45 (m, 2H), 7.38-7.34 (m, 1H), 7.28 (d, J=7.7 Hz, 1H, 6.97 (dd, J=8.5, 2.1 Hz, 1H), 6.54 (d, J=5.6 Hz, 1H), 6.32 (s, 1H), 4.97 (d, J=5.2 Hz, 1H), 3.96 (s, 3H), 3.88 (d, J=3.4 Hz, 1H), 3.45 (s, 3H), 3.38-3.33 (m, 1H), 2.75 (d, J=3.9 Hz, 1H), 2.40 (dd, J=11.9, 5.8 Hz, 1H), 2.34 (s, 3H), 1.59 (s, 3H)

$^{13}$C NMR (151 MHZ, Methanol-$d_4$) δ 175.7, 159.4, 142.2, 138.2, 134.1, 133.1, 131.8, 128.2, 126.9, 126.2, 124.5, 122.4, 120.4, 116.6, 115.6, 114.4, 109.9, 108.8, 100.8, 93.2, 84.5, 82.1, 58.5, 56.2, 52.7, 47.1, 33.4, 30.8, 29.9.

Regiochemistry and major product assigned by comparison of $^1$H NMR in Chloroform-d of the mixture to reported spectra of TAN-999.[1]

+ESI-HRMS m/z: calc'd for [M+H]$^+$ $C_{29}H_{29}N_4O_4$=497.2183, found $C_{29}H_{29}N_4O_4$=497.2183.

FTIR (Thin Film): 3337, 2918, 2850, 2333, 1677, 1588, 1559, 1466, 1420, 1351, 1319, 1292, 1209, 1128, 1038, 802, 751, 724

Figure 12:
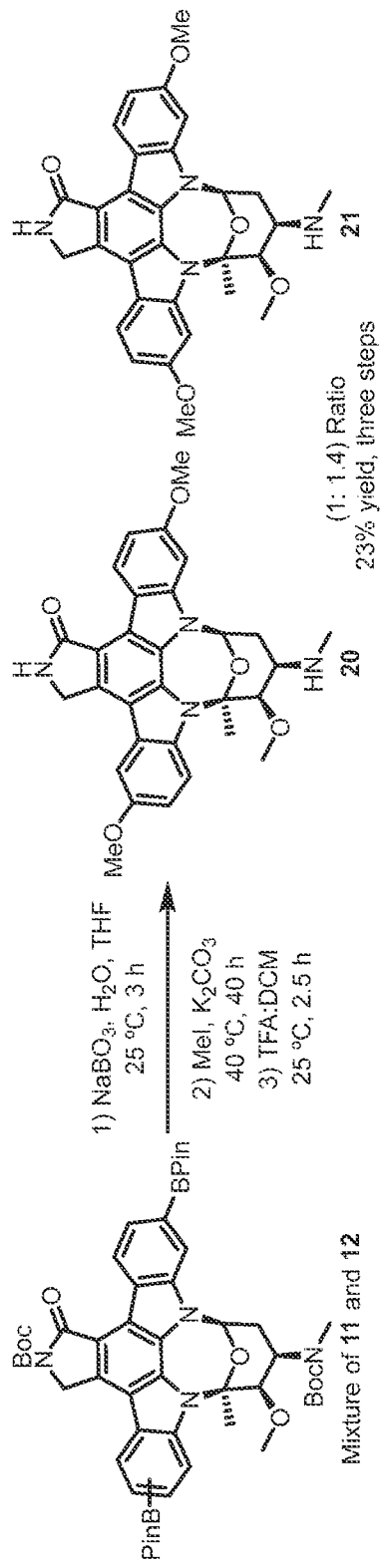

Preparation of Bis-Methyl Ethers 20 and 21:

FIG. 12 shows a synthetic scheme for the preparation of Bis-methyl esters 20 and 21 from a mixture of 11 and 12.

To 1.5 dram vial was added a mixture of 11 and 12 (22.5 mg, 0.025 mmol, 1 equiv) as a solution in THF (1 mL), followed by the addition of $NaBO_3 \cdot 4 H_2O$ (15.4 mg, 0.10 mmol, 4.5 equiv) and $H_2O$ (1 mL) and stirred at 25° C. for 3 h and reaction was diluted with $H_2O$, extracted with DCM, and organic layers were dried with $Na_2SO_4$. Half of the crude mixture was taken forward without further purification.

To a flame dried 1.5 dram vial under an atmosphere of nitrogen was added the crude mixture as a solution in THF (0.5 mL) followed by addition of $K_2CO_3$ (20.0 mg, 0.12 mmol, 12 equiv) and MeI (7.5 L, 0.018 mmol, 10 equiv) and was heated to 40° C. for 45 h, and allowed to cool followed by evaporation of volatiles. Reaction was dissolved in DCM, washed with water, and aqueous layer was extracted with DCM. Organic layers were dried with $Na_2SO_4$.

The crude mixture was taken forward without further purification.

The above mixture was dissolved in DCM (150 μL), to which TFA (100 μL) was added and stirred for 16 h, and volatiles were evaporated. The mixture was purified using silica flash column chromatography using 0:100 to 5:95 to 10:90 MeOH:DCM. To provide a 1:1.4 ratio of 20:21.

$^1$H NMR (600 MHZ, Methanol-$d_4$) δ 9.06 (d, J=8.5 Hz, 1H), 7.81 (d, J=8.5 Hz, 1H), 7.51 (d, J=2.2 Hz, 1H), 6.96 (dd, J=8.5, 2.2 Hz, 1H), 6.93-6.87 (m, 2H), 6.58 (d, J=6.7 Hz, 2H), 4.94 (d, J=2.7 Hz, 2H), 4.06 (d, J=3.4 Hz, 1H), 3.95 (s, 3H), 3.94 (s, 3H), 3.24 (d, J=4.6 Hz, 3H), 3.16 (d, J=4.4 Hz, 1H), 2.66-2.60 (m, 2H), 2.37 (s, 2H), 2.36 (s, 1H), 1.89 (s, 1H), 1.82 (s, 3H).

$^{13}$C NMR (151 MHZ, Methanol-$d_4$) δ 175.8, 160.2, 159.3, 142.1, 139.4, 135.7, 131.7, 127.8, 119.9, 118.4, 116.3, 116.1, 114.9, 114.5, 114.1, 109.6, 109.4, 105.0, 100.7, 92.9, 84.4, 82.1, 58.6, 56.3, 56.1, 52.9, 47.1, 33.4, 30.8, 30.0.

Regiochemistry and major product assigned by NOESY.

+ESI-HRMS m/z: calc'd for [M+Na]$^+$ $C_{30}H_{31}N_4O_5Na^+$=527.2289, found $C_{30}H_{31}N_4O_5Na^+$=527.2288.

FTIR (Thin Film): 3335, 2925, 2852, 1675, 1623, 1590, 1493, 1464, 1421, 1355, 1323, 1290, 1249, 1218, 1170, 1127, 1034, 858, 818, 628

$^1$H NMR (600 MHZ, Methanol-$d_4$) δ 9.08 (d, 1H), 7.89 (d, J=9.1 Hz, 1H), 7.38 (d, J=2.8 Hz, 1H), 7.06 (dd, J=9.2, 2.6 Hz, 1H), 6.96 (dd, J=8.5, 2.2 Hz, 1H), 6.93-6.87 (m, 2H), 6.58 (d, J=6.7 Hz, 2H), 4.99 (s, 2H), 4.02 (d, J=3.4 Hz, 1H), 3.95 (s, 3H), 3.94 (s, 3H), 3.24 (d, J=4.6 Hz, 2H), 3.16 (d, J=4.4 Hz, 1H), 2.57-2.51 (m, 2H), 2.37 (s, 2H), 2.36 (s, 1H), 1.89 (s, 1H), 1.82 (s, 3H)

$^{13}$C NMR (151 MHZ, Methanol-$d_4$) δ 175.8, 160.2, 159.3, 142.1, 139.4, 132.8, 131.7, 127.7, 122.2, 118.4, 116.4, 116.1, 114.9, 114.5, 114.1, 109.6, 109.2, 104.6, 100.7, 93.2, 84.5, 82.1, 58.6, 56.2, 56.1, 52.7, 47.1, 33.5, 31.0, 29.8.

Regiochemistry and major product assigned by NOESY.

+ESI-HRMS m/z: calc'd for [M+Na]$^+$ $C_{30}H_{31}N_4O_5Na^+$=527.2289, found $C_{30}H_{31}N_4O_5Na^+$=527.2288.

FTIR (Thin Film): 3335, 2925, 2852, 1675, 1623, 1590, 1493, 1464, 1421, 1355, 1323, 1290, 1249, 1218, 1170, 1127, 1034, 858, 818, 628

Figure 13:
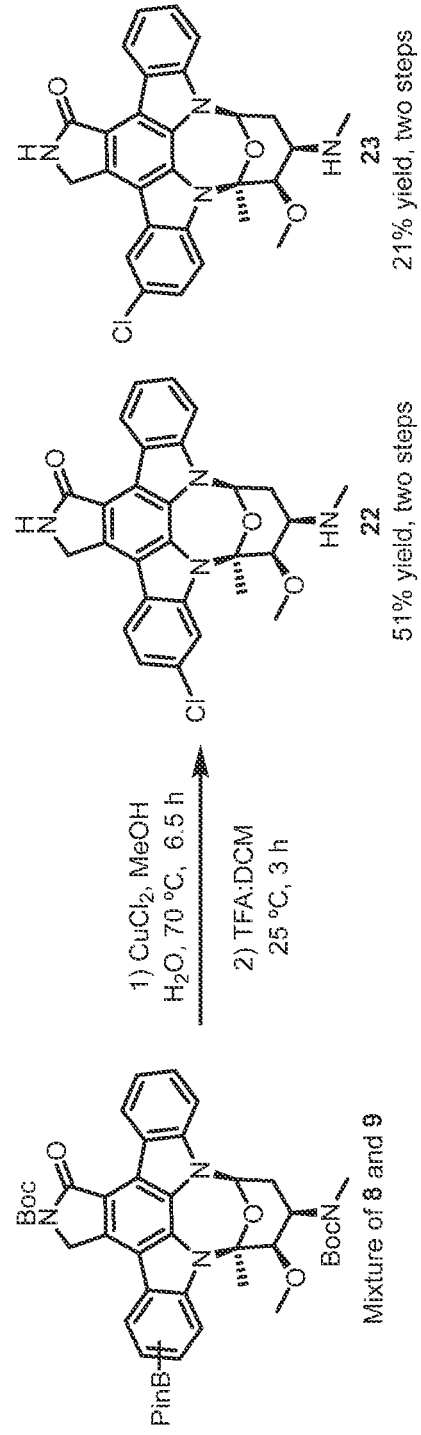

Preparation of Chlorides 22 and 23:

FIG. 13 shows a synthetic scheme for the preparation of Chlorides 22 and 23 from a mixture of 8 and 9.

To 1.5 dram vial was added a mixture of 8 and 9 (18.0 mg, 0.023 mmol, 1 equiv) as a solution in MeOH (0.5 mL), followed by the addition of $CuCl_2$ (30.9 mg, 0.23 mmol, 10 equiv) and $H_2O$ (0.5 mL) and heated to 70° C. for 6.5 h and reaction was diluted with $H_2O$, extracted with DCM, and organic layers were dried with $Na_2SO_4$. Crude material was initially purified using silica flash column chromatography using 60:40 to 100:0 EtOAc:Hex gradient. Separation of the two isomers was performed using NP-HPLC using an isocratic 80:20 EtOAc:Hex solvent system, to provide two separate isomers whose regiochmiestry could not be assigned until Boc deprotection.

To each of the above isomers was dissolved in DCM (250 µL), to which TFA (100 µL) was added and stirred for 2.5 h, and volatiles were evaporated. Crude material was purified using silica flash column chromatography using 0:100 to 5:95 MeOH:DCM.

Purification provided 2.3 mg of 22 as a yellow solid. Analytical sample was chromatographed using 20:80 to 100:0 Acetone Hexane to provide a white solid.

$^1$H NMR (400 MHZ, Methanol-$d_4$) δ 9.26 (d, J=8.3 Hz, 1H), 8.00 (d, J=9.1 Hz, 1H), 7.92 (d, J=2.3 Hz, 1H), 7.51-7.47 (m, 2H), 7.40 (dd, J=9.2, 2.0 Hz, 1H), 7.31-7.27 (m, 1H), 6.69-6.66 (m, 1H), 5.01 (d, J=1.8 Hz, 2H), 4.06 (d, J=3.3 Hz, 1H), 2.65-2.59 (m, 2H), 2.37 (s, 3H), 2.16 (s, 3H), 1.67 (s, 3H).

*Note Doublet with integration of 1H is eclipsed by Methanol-$d_4$ peak.

$^{13}$C NMR (151 MHZ, Methanol-$d_4$) δ 175.4, 138.2, 133.9, 132.8, 127.1, 126.9, 126.8, 126.6, 125.5, 124.3, 121.1, 120.6, 120.0, 119.2, 117.3, 117.2, 116.8, 114.4, 109.0, 93.3, 84.3, 82.0, 58.4, 47.1, 33.3, 33.1, 30.1.

Regiochemistry assigned by combination of 1H and NOESY provided and comparison to chloride 23.

+ESI-HRMS m/z: calc'd for [M+H]$^+$ $C_{28}H_{26}ClN_4O_3^+$=501.1688, found $C_{28}H_{26}ClN_4O_3^+$=501.1699.

FTIR (Thin Film): 3330, 2334, 1683, 1454, 1399, 1321, 1279, 1207, 1146, 849, 803, 749, 726

Purification provided 5.9 mg of 23 as a yellow solid. Analytical sample was chromatographed using 20:80 to 100:0 Acetone Hexane to provide a white solid.

$^1$H NMR (400 MHZ, Methanol-$d_4$) δ 9.25 (d, J=8.0 Hz, 1H), 8.01 (d, J=1.8 Hz, 1H), 7.91 (d, J=8.4 Hz, 1H), 7.50-7.44 (m, 2H), 7.32-7.25 (m, 2H), 6.65 (dd, J=5.2, 2.8 Hz, 1H), 5.00-4.97 (m, 2H), 4.07 (d, J=3.5 Hz, 1H), 3.37 (d, J=3.8 Hz, 1H), 2.65-2.58 (m, 2H), 2.36 (s, 3H), 2.16 (s, 3H), 1.67 (s, 3H).

$^{13}$C NMR (151 MHZ, Methanol-$d_4$) δ 175.4, 141.5, 138.3, 133.6, 132.5, 131.3, 128.7, 127.1, 126.6, 126.5, 124.4, 124.3, 122.6, 121.5, 120.5, 120.0, 116.6, 116.1, 108.9, 93.1, 84.7, 82.0, 58.0, 52.1, 47.1, 33.5, 31.0, 30.1.

Regiochemistry assigned by combination of 1H and NOESY provided and comparison to chloride 22.

+ESI-HRMS m/z: calc'd for [M+H]$^+$ $C_{28}H_{26}ClN_4O_3^+$=501.1688, found $C_{28}H_{26}ClN_4O_3^+$=501.1697.

FTIR (Thin Film): 3357, 2180, 1975, 1682, 1460, 1315, 1207, 1140, 847, 803, 726, 427

Figure 14:
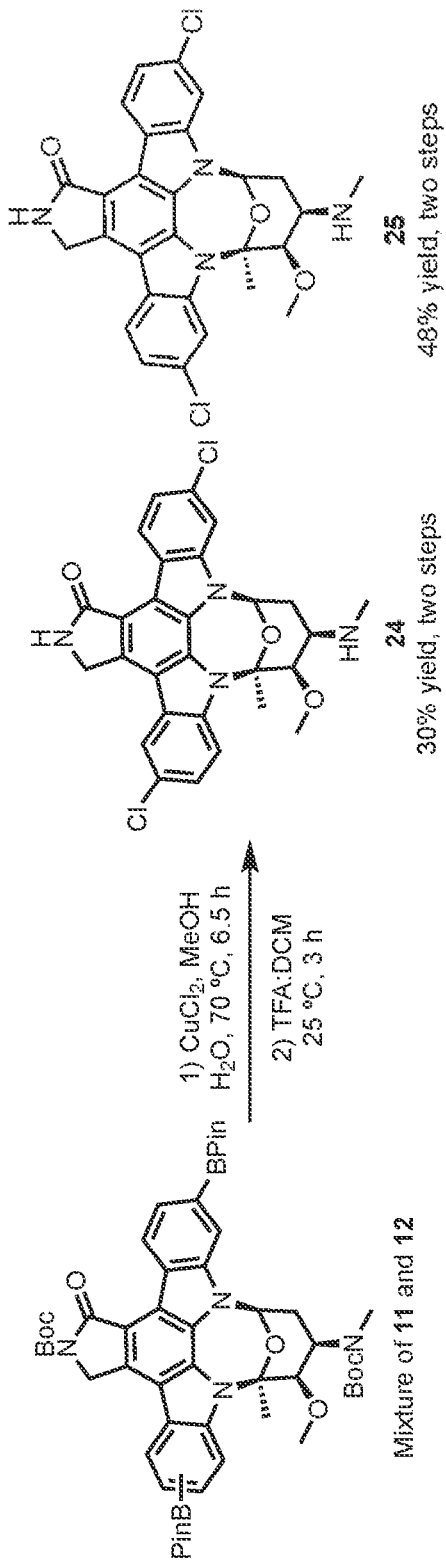

Preparation of Bis-Chlorides 24 and 25:

FIG. 14 shows a synthetic scheme for the preparation of Bis-Chlorides 24 and 25 from a mixture of 11 and 12.

To 1.5 dram vial was added a mixture of 11 and 12 (22.5 mg, 0.025 mmol, 1 equiv) as a solution in MeOH (0.5 mL), followed by the addition of $CuCl_2$ (67.2 mg, 0.5 mmol, 20 equiv) and $H_2O$ (0.5 mL) and heated to 70° C. for 6.5 h and reaction was diluted with $H_2O$, extracted with DCM, and organic layers were dried with $Na_2SO_4$. Separation of the two isomers was performed using NP-HPLC using an isocratic 80:20 EtOAc:Hex solvent system, to provide two separate isomers whose regiochemistry could not be assigned until Boc deprotection.

Each of the above isomers was dissolved in DCM (250 µL), to which TFA (100 µL) was added and stirred for 2.5 h, and volatiles were evaporated. Crude material was purified using silica flash column chromatography using 0:100 to 5:95 MeOH:DCM.

Purification provided 4.0 mg of 24 as a yellow solid. Analytical Sample was purified using silica flash column chromatography 20:80 to 100 Acetone Hexane.

$^1$H NMR (400 MHZ, Methanol-$d_4$) δ 9.20 (d, J=8.5 Hz, 1H), 7.99 (d, J=9.4 Hz, 1H), 7.91 (d, J=2.4 Hz, 1H), 7.58-7.53 (m, 1H), 7.40 (dd, J=9.2, 2.0 Hz, 1H), 7.25 (dd, J=8.6, 1.7 Hz, 1H), 6.64-6.61 (m, 1H), 5.00 (d, J=1.0 Hz, 2H), 4.04 (d, J=3.1 Hz, 1H), 2.61-2.57 (m, 2H), 2.36 (s, 3H), 2.16 (s, 3H), 1.90 (s, 1H), 1.65 (s, 3H).

*Note Doublet with integration of 1H is eclipsed by Methanol-$d_4$ peak.

$^{13}$C NMR (151 MHZ, Methanol-$d_4$) δ 174.9, 138.8, 138.2, 134.1, 132.3, 132.1, 128.4, 127.9, 126.9, 126.7, 125.8, 122.7, 121.3, 120.8, 119.7, 116.4, 116.0, 114.6, 109.1, 93.5, 83.7, 82.0, 58.8, 53.2, 47.0, 32.9, 30.3, 29.8.

Regiochemistry assigned by NOESY.

+ESI-HRMS m/z: calc'd for [M+H]$^+$ $C_{28}H_{25}Cl_2N_4O_3^+$=535.1298, found $C_{28}H_{25}Cl_2N_4O_3^+$=535.1310.

FTIR (Thin Film): 3358, 2045, 2014, 1975, 1684, 1636, 1457, 1207, 1145, 848, 803, 726

Purification provided 6.4 mg of 25 as a yellow solid. Analytical sample was chromatographed using 20:80 to 100:0 Acetone Hexane to provide a white solid.

$^1$H NMR (600 MHZ, Methanol-$d_4$) δ 9.04 (d, J=8.5 Hz, 1H), 7.92 (d, J=1.6 Hz, 1H), 7.78 (d, J=8.3 Hz, 1H), 7.37 (d, J=1.6 Hz, 1H), 7.27 (dd, J=8.3, 1.6 Hz, 1H), 7.11 (d, J=8.5 Hz, 1H), 6.53 (dd, J=6.8, 1.7 Hz, 1H), 4.84 (s, 3H), 4.59 (s, 3H), 4.00 (d, J=3.1 Hz, 1H), 3.04 (s, 3H), 2.66-2.59 (m, 1H), 2.40 (d, J=4.9 Hz, 1H), 2.39-2.36 (m, 1H), 2.35 (s, 3H), 1.77 (s, 3H).

$^{13}$C NMR (151 MHZ, Methanol-$d_4$) δ 175.0, 141.1, 138.4, 133.9, 132.2, 132.0, 131.5, 128.6, 127.9, 124.2, 122.8, 121.6, 120.7, 119.8, 119.2, 117.2, 115.9, 115.6, 115.0, 109.0, 93.2, 84.1, 82.0, 58.4, 52.5, 47.1, 33.2, 30.65, 29.9.

Regiochemistry assigned by NOESY.

+ESI-HRMS m/z: calc'd for [M+H]$^+$ $C_{28}H_{25}Cl_2N_4O_3{}^+$=535.1298, found $C_{28}H_{25}Cl_2N_4O_3{}^+$=535.1309.

FTIR (Thin Film): 3335, 2176, 2045, 1974, 1682, 1457, 1313, 1207, 1141, 847, 726

Example 2

Biological assays of representative staurosporine analogs are described in this example.

As discussed above, over one-thousand semisynthetic analogs of ICZs have been assayed for activity since the original isolation of staurosporine and among these many have been produced via electrophilic aromatic substitution, which only provides access to functionality at C3 and C9. The only known example of a staurosporine analog functionalized elsewhere on the aromatic indolocarbazole core is the natural product TAN-999 (19), which possesses a methoxy substituent at C10. To date, detailed biological studies of 19 reported in the open literature have been focused on its immunomodulatory activity in macrophages and a brief notation that it inhibits protein kinase C. The cytotoxicity of staurosporine and phenol analogs 13 and 14 against MDA-MB-231 and HMLE breast cancer cell lines was investigated.

Solid compounds were re-suspended in DMSO to yield a final concentration of 5 mM and aliquots were stored at −80° C. MDA-MB-231 cells were plated on 96-well plates with 2,000 cells per well in DMEM media with 10% FBS. After 24 h, compounds were added to media and allowed to incubate for 72 h at 37° C., 5% CO2. Relative cell metabolic activity was assessed by incubation with MTS assay reagent for 3 h (CellTiter 96 Aqueous One Solution Cell Proliferation Assay, Promega) according to the manufacturer's protocol. Background absorbance (media only) was subtracted from all other wells and absorbance was then normalized to DMSO treatment at matching concentrations. The normalized relative viability values were graphed against the drug dosage and IC$_{50}$ (drug concentration eliciting 50% of the maximum inhibition) values were calculated for each tested cell line using the "log(inhibitor) vs. response—Variable slope" function in Prism6 (Graphpad).

The inclusion of a phenol at either the C9 or C10 position of staurosporine retained its cytotoxicity against MDA-MB-231 cell line. Against the HMLE cell line the phenolic analogs were slightly less potent with 9-OH staurosporine (13) being 5.6-fold less active and 10-OH staurosporine (14) being 12.0-fold less potent. Table 2 below shows the cytotoxic activity of staurosporine and phenol analogs 13 and 14.

TABLE 2

| Compound | MDA-MB-231 | | HMLE | |
|---|---|---|---|---|
| | IC$_{50}$ (nM) | SD | IC$_{50}$ (nM) | SD |
| Staurosporine | 2.5 | ±0.2 | 4.9 | ±0.4 |
| 13 | 2.0 | n.d. | 27.5 | ±10.8 |
| 14 | 3.4 | ±1.3 | 58.7 | ±20.1 |

What is claimed is:

1. A method for synthesizing staurosporine analogs, comprising:
   reacting staurosporine with Boc$_2$O to produce Bis-Boc staurosporine, wherein Boc is tert-Butyloxycarbonyl;
   reacting the Bis-Bos staurosporine with B$_2$Pin$_2$ to produce boron pinacol esters of Bis-Boc staurosporine, wherein B$_2$Pin$_2$ is bis(pinacolato)diboron;
   oxidizing or chlorinating the boron pinacol esters of Bis-Boc staurosporine to produce staurosporine analog intermediates; and
   deprotecting the staurosporine analog intermediates to remove Boc to produce the staurosporine analogs.

2. The method of claim 1, further comprising a step of methylation of at least one phenol in the staurosporine analog intermediates.

3. The method of claim 1, wherein the Bis-Boc staurosporine has a structure of:

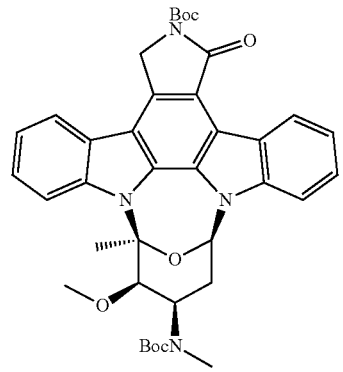

4. The method of claim 1, wherein the boron pinacol esters of Bis-Boc staurosporine have a structure of:

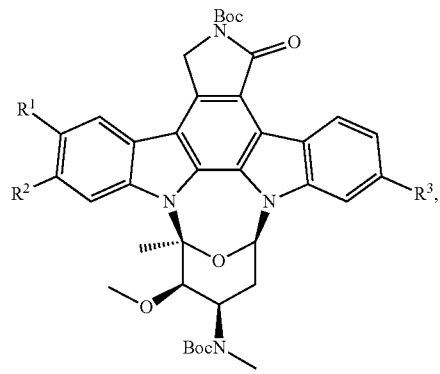

wherein R$^1$, R$^2$, and R$^3$ are independently BPin or H, wherein BPin is pinacolato borane.

5. The method of claim 1, wherein the staurosporine analog intermediates have a structure of:
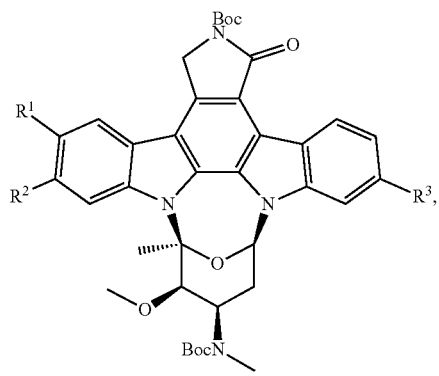
wherein $R^1$, $R^2$, and $R^3$ are independently OH or Cl.
6. The method of claim 1, wherein the staurosporine analogs have a structure of:
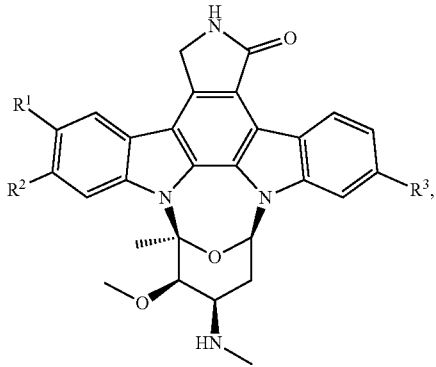
wherein $R^1$, $R^2$, and $R^3$ are independently OH, OMe, or Cl.
* * * * *

UNITED STATES PATENT AND TRADEMARK OFFICE
CERTIFICATE OF CORRECTION

PATENT NO. : 12,173,012 B2
APPLICATION NO. : 18/422175
DATED : December 24, 2024
INVENTOR(S) : John L. Wood et al.

It is certified that error appears in the above-identified patent and that said Letters Patent is hereby corrected as shown below:

In the Specification

1. In Column 1, Line 7, delete "2021," and insert -- 2021, now U.S. Pat. No. 11,993,611, --, therefor.

2. In Column 1, Line 31, delete "indolocabazole-containing" and insert -- indolocarbazole-containing --, therefor.

3. In Column 2, Line 1, delete "over" and insert -- of over --, therefor.

4. In Column 3, Line 28, delete "toward to" and insert -- toward --, therefor.

5. In Column 4, Line 17, delete "$R_1$, $R_2$, and $R_3$" and insert -- $R^1$, $R^2$, and $R^3$ --, therefor.

6. In Column 5, Line 34, delete "Bis-Bos" and insert -- Bis-Boc --, therefor.

7. In Column 5, Lines 49-50, delete "isoethonic" and insert -- isotonic --, therefor.

8. In Column 7, Line 40, delete "the" and insert -- to the --, therefor.

9. In Column 7, Line 54, delete "1H" and insert -- $^1$H --, therefor.

10. In Column 7, Line 57, delete "1H" and insert -- $^1$H --, therefor.

11. In Column 7, Line 59, delete "MHZ," and insert -- MHz, --, therefore at each occurrence throughout the patent.

12. In Column 8, Line 62, delete "[M+Na]+" and insert -- [M+Na]$^+$ --, therefor.

13. In Column 9, Line 6, delete "$NaBO_3$·4 $H_2O$" and insert -- $NaBO_3$·$4H_2O$ --, therefor.

Signed and Sealed this
Fifteenth Day of April, 2025

Coke Morgan Stewart
*Acting Director of the United States Patent and Trademark Office*

CERTIFICATE OF CORRECTION (continued)
U.S. Pat. No. 12,173,012 B2

14. In Column 9, Line 32, delete "1H" and insert -- $^1$H --, therefor.

15. In Column 9, Line 64, delete "NaBO$_3$·4 H$_2$O" and insert -- NaBO$_3$·4H$_2$O --, therefor.

16. In Column 10, Line 2, delete "stating" and insert -- starting --, therefor.

17. In Column 10, Line 31, delete "NaBO$_3$·4 H$_2$O" and insert -- NaBO$_3$·4H$_2$O --, therefor.

18. In Column 10, Line 60, delete "C$_{28}$H$_{27}$N$_4$O$_5$+" and insert -- C$_{28}$H$_{27}$N$_4$O$_5^+$ --, therefor.

19. In Column 11, Line 22, delete "NaBO$_3$·4 H$_2$O" and insert -- NaBO$_3$·4H$_2$O --, therefor.

20. In Column 11, Line 45, delete "1H),)," and insert -- 1H), --, therefor.

21. In Column 11, Line 54, delete "1H," and insert -- 1H), --, therefor.

22. In Column 12, Line 14, delete "1H," and insert -- 1H), --, therefor.

23. In Column 12, Line 36, delete "NaBO$_3$·4 H$_2$O" and insert -- NaBO$_3$·4H$_2$O --, therefor.

24. In Column 12, Line 45, delete "(7.5 L," and insert -- (7.5 µL, --, therefor.

25. In Column 13, Line 37, delete "regiochmiestry" and insert -- regiochemistry --, therefor.

26. In Column 13, Line 59, delete "1H" and insert -- $^1$H --, therefor.

27. In Column 14, Line 12, delete "1H" and insert -- $^1$H --, therefor.

In the Claims

28. In Column 16, Line 7, in Claim 1, delete "Bis-Bos" and insert -- Bis-Boc --, therefor.